(12) United States Patent
Onishi

(10) Patent No.: US 9,234,217 B2
(45) Date of Patent: Jan. 12, 2016

(54) METHOD FOR PRODUCING ISOBUTANOL AND RECOMBINANT MICROORGANISM CAPABLE OF PRODUCING ISOBUTANOL

(71) Applicant: TOYOTA JIDOSHA KABUSHIKI KAISHA, Toyota-shi, Aichi (JP)

(72) Inventor: Toru Onishi, Toyota (JP)

(73) Assignee: TOYOTA JIDOSHA KABUSHIKI KAISHA, Aichi (JP)

( * ) Notice: Subject to any disclaimer, the term of this patent is extended or adjusted under 35 U.S.C. 154(b) by 46 days.

(21) Appl. No.: 14/235,634

(22) PCT Filed: Oct. 23, 2012

(86) PCT No.: PCT/JP2012/006764
§ 371 (c)(1),
(2) Date: Jan. 28, 2014

(87) PCT Pub. No.: WO2013/061571
PCT Pub. Date: May 2, 2013

(65) Prior Publication Data
US 2014/0170722 A1    Jun. 19, 2014

(30) Foreign Application Priority Data

Oct. 24, 2011 (JP) ................................. 2011-233268

(51) Int. Cl.
| | |
|---|---|
| *C12P 7/16* | (2006.01) |
| *C12N 9/04* | (2006.01) |
| *C12N 15/00* | (2006.01) |
| *C12N 1/20* | (2006.01) |
| *C12N 1/14* | (2006.01) |
| *C07H 21/04* | (2006.01) |
| *C12N 15/81* | (2006.01) |

(52) U.S. Cl.
CPC ................ *C12P 7/16* (2013.01); *C12N 9/0006* (2013.01); *C12N 15/81* (2013.01); *C12Y 101/01042* (2013.01); *C07K 2319/07* (2013.01); *Y02E 50/10* (2013.01)

(58) Field of Classification Search
CPC .......... C12N 9/0006; C12N 15/81; C12P 7/16
See application file for complete search history.

(56) References Cited

U.S. PATENT DOCUMENTS

| | | | | |
|---|---|---|---|---|
| 7,851,188 B2 * | 12/2010 | Donaldson et al. | ........... | 435/160 |
| 2007/0092957 A1 | 4/2007 | Donaldson et al. | | |
| 2010/0129886 A1 * | 5/2010 | Anthony et al. | ............. | 435/160 |

FOREIGN PATENT DOCUMENTS

| | | |
|---|---|---|
| JP | 2009-513136 A | 4/2009 |
| WO | 2009/085953 A2 | 7/2009 |
| WO | 2010/051527 A2 | 5/2010 |

OTHER PUBLICATIONS

Verho et al. Engineering redox cofactor regeneration for improved pentose fermentation in *Saccharomyces cerevisiae*. Appl Environ Microbiol. Oct. 2003;69(10):5892-7.*
International Search Report for PCT/JP2012/006764 dated Feb. 4, 2013.
Karyl I. Minard et al., "Sources of NADPH+ and Expression of Mammalian NADP—specific Isocitrate Dehydrogenases in *Saccharomyces cerevisiae*", The Journal of Biological Chemistry, Nov. 20, 1998, pp. 31486-31493, vol. 273, No. 47.
Veronica Contreras-Shannon et al., "Kinetic Properties and Metabolic Contributions of Yeast Mitochondrial and Cytosolic NADP+— specific Isocitrate Dehydrogenases", The Journal of Biological Chemistry, Feb. 11, 2005, pp. 4469-4475, vol. 280, No. 6.
Veronica Contreras-Shannon et al.,"Influence of compartmental localization on the function of yeast NADP+—specific isocitrate dehydrogenases", Archives of Biochemistry and Biophysics, 2004, pp. 235-246, vol. 423.

* cited by examiner

*Primary Examiner* — Yong Pak
(74) *Attorney, Agent, or Firm* — Sughrue Mion, PLLC

(57) ABSTRACT

This invention is intended to produce isobutanol with excellent productivity via a fermentation process. A reaction in which NADP-dependent isocitrate dehydrogenase generates NADPH from NADP is used as a source of NADPH for the reaction of converting 2-acetolactate into 2,3-dihydroxy-isovalerate in the isobutanol biosynthesis pathway.

2 Claims, 2 Drawing Sheets

SEQUENCE LISTING

```
<160> NUMBER OF SEQ ID NOS: 89

<210> SEQ ID NO 1
<211> LENGTH: 1110
<212> TYPE: DNA
<213> ORGANISM: Saccharomyces cerevisiae
<220> FEATURE:
<221> NAME/KEY: CDS
<222> LOCATION: (1)..(1110)

<400> SEQUENCE: 1 atg ttg aga aat act ttt ttt aga aac acc tcg agg agg ttt ttg gct      48
Met Leu Arg Asn Thr Phe Phe Arg Asn Thr Ser Arg Arg Phe Leu Ala
1               5                   10                  15 act gta aag caa cct tca atc gga aga tat acc ggc aaa cct aac cct      96
Thr Val Lys Gln Pro Ser Ile Gly Arg Tyr Thr Gly Lys Pro Asn Pro
            20                  25                  30 tct acc ggc aaa tac acg gtc tcg ttc att gaa ggt gat ggt atc gga     144
Ser Thr Gly Lys Tyr Thr Val Ser Phe Ile Glu Gly Asp Gly Ile Gly
        35                  40                  45 cct gaa att tcc aag tct gta aag aaa atc ttt agt gca gca aac gtc     192
Pro Glu Ile Ser Lys Ser Val Lys Lys Ile Phe Ser Ala Ala Asn Val
    50                  55                  60
```

```
ccc ata gaa tgg gaa tct tgt gat gtt agc cct atc ttt gtc aac gga      240
Pro Ile Glu Trp Glu Ser Cys Asp Val Ser Pro Ile Phe Val Asn Gly
 65              70                  75                  80 tta acg acc att cct gac cct gcc gta caa tct atc aca aaa aac ctg      288
Leu Thr Thr Ile Pro Asp Pro Ala Val Gln Ser Ile Thr Lys Asn Leu
                 85                  90                  95 gtt gca cta aaa ggt cca cta gct aca cct att ggt aaa ggt cac aga      336
Val Ala Leu Lys Gly Pro Leu Ala Thr Pro Ile Gly Lys Gly His Arg
            100                 105                 110 tct ttg aat ttg aca ttg aga aaa aca ttt ggg tta ttt gcc aac gtt      384
Ser Leu Asn Leu Thr Leu Arg Lys Thr Phe Gly Leu Phe Ala Asn Val
        115                 120                 125 cgt ccc gca aag tct att gaa ggt ttt aag acc act tac gaa aac gtt      432
Arg Pro Ala Lys Ser Ile Glu Gly Phe Lys Thr Thr Tyr Glu Asn Val
    130                 135                 140 gat tta gtt ctt atc aga gag aat acc gaa ggt gaa tat tct ggt atc      480
Asp Leu Val Leu Ile Arg Glu Asn Thr Glu Gly Glu Tyr Ser Gly Ile
145                 150                 155                 160 gaa cac ata gtt tgc cct ggc gtt gtt caa tct att aaa ctg atc aca      528
Glu His Ile Val Cys Pro Gly Val Val Gln Ser Ile Lys Leu Ile Thr
                165                 170                 175 aga gat gcc tct gag cga gtc att aga tac gct ttt gaa tat gca aga      576
Arg Asp Ala Ser Glu Arg Val Ile Arg Tyr Ala Phe Glu Tyr Ala Arg
            180                 185                 190 gcc atc ggc aga cca aga gtt att gtg gta cat aaa tct act atc cag      624
Ala Ile Gly Arg Pro Arg Val Ile Val Val His Lys Ser Thr Ile Gln
        195                 200                 205 aga tta gct gat ggt tta ttc gtt aat gtt gcc aaa gaa cta tcc aaa      672
Arg Leu Ala Asp Gly Leu Phe Val Asn Val Ala Lys Glu Leu Ser Lys
    210                 215                 220 gag tat cct gac ctt act tta gaa act gaa ctt att gat aac agt gtg      720
Glu Tyr Pro Asp Leu Thr Leu Glu Thr Glu Leu Ile Asp Asn Ser Val
225                 230                 235                 240 tta aag gtg gtc acc aac cca tct gct tac aca gac gct gtt tct gtt      768
Leu Lys Val Val Thr Asn Pro Ser Ala Tyr Thr Asp Ala Val Ser Val
                245                 250                 255 tgt cca aat cta tac ggt gat atc ttg tcc gac ttg aac tct ggt ttg      816
Cys Pro Asn Leu Tyr Gly Asp Ile Leu Ser Asp Leu Asn Ser Gly Leu
            260                 265                 270 agc gcc ggt tct tta ggt tta act cca tct gcc aat att ggt cat aaa      864
Ser Ala Gly Ser Leu Gly Leu Thr Pro Ser Ala Asn Ile Gly His Lys
        275                 280                 285 atc tcg atc ttt gaa gct gtc cat ggc tct gcc cct gat att gcc ggt      912
Ile Ser Ile Phe Glu Ala Val His Gly Ser Ala Pro Asp Ile Ala Gly
    290                 295                 300 caa gat aaa gcg aat cca act gcc cta ctt tta tct tca gta atg atg      960
Gln Asp Lys Ala Asn Pro Thr Ala Leu Leu Leu Ser Ser Val Met Met
305                 310                 315                 320 tta aac cac atg ggt cta acg aat cat gct gac caa att caa aat gca     1008
Leu Asn His Met Gly Leu Thr Asn His Ala Asp Gln Ile Gln Asn Ala
                325                 330                 335 gta ttg tct act atc gca tca ggt cca gaa aac aga aca ggt gac ttg     1056
Val Leu Ser Thr Ile Ala Ser Gly Pro Glu Asn Arg Thr Gly Asp Leu
            340                 345                 350 gct ggt act gct act act tca tca ttc act gaa gca gtc atc aag aga     1104
Ala Gly Thr Ala Thr Thr Ser Ser Phe Thr Glu Ala Val Ile Lys Arg
        355                 360                 365 tta taa                                                              1110
Leu
```

```
<210> SEQ ID NO 2
<211> LENGTH: 369
<212> TYPE: PRT
<213> ORGANISM: Saccharomyces cerevisiae

<400> SEQUENCE: 2
```

Met Leu Arg Asn Thr Phe Phe Arg Asn Thr Ser Arg Arg Phe Leu Ala
1               5                   10                  15

Thr Val Lys Gln Pro Ser Ile Gly Arg Tyr Thr Gly Lys Pro Asn Pro
            20                  25                  30

Ser Thr Gly Lys Tyr Thr Val Ser Phe Ile Glu Gly Asp Gly Ile Gly
        35                  40                  45

Pro Glu Ile Ser Lys Ser Val Lys Lys Ile Phe Ser Ala Ala Asn Val
    50                  55                  60

Pro Ile Glu Trp Glu Ser Cys Asp Val Ser Pro Ile Phe Val Asn Gly
65                  70                  75                  80

Leu Thr Thr Ile Pro Asp Pro Ala Val Gln Ser Ile Thr Lys Asn Leu
                85                  90                  95

Val Ala Leu Lys Gly Pro Leu Ala Thr Pro Ile Gly Lys Gly His Arg
            100                 105                 110

Ser Leu Asn Leu Thr Leu Arg Lys Thr Phe Gly Leu Phe Ala Asn Val
        115                 120                 125

Arg Pro Ala Lys Ser Ile Glu Gly Phe Lys Thr Thr Tyr Glu Asn Val
    130                 135                 140

Asp Leu Val Leu Ile Arg Glu Asn Thr Glu Gly Glu Tyr Ser Gly Ile
145                 150                 155                 160

Glu His Ile Val Cys Pro Gly Val Val Gln Ser Ile Lys Leu Ile Thr
                165                 170                 175

Arg Asp Ala Ser Glu Arg Val Ile Arg Tyr Ala Phe Glu Tyr Ala Arg
            180                 185                 190

Ala Ile Gly Arg Pro Arg Val Ile Val His Lys Ser Thr Ile Gln
        195                 200                 205

Arg Leu Ala Asp Gly Leu Phe Val Asn Val Ala Lys Glu Leu Ser Lys
    210                 215                 220

Glu Tyr Pro Asp Leu Thr Leu Glu Thr Glu Leu Ile Asp Asn Ser Val
225                 230                 235                 240

Leu Lys Val Val Thr Asn Pro Ser Ala Tyr Thr Asp Ala Val Ser Val
                245                 250                 255

Cys Pro Asn Leu Tyr Gly Asp Ile Leu Ser Asp Leu Asn Ser Gly Leu
            260                 265                 270

Ser Ala Gly Ser Leu Gly Leu Thr Pro Ser Ala Asn Ile Gly His Lys
        275                 280                 285

Ile Ser Ile Phe Glu Ala Val His Gly Ser Ala Pro Asp Ile Ala Gly
    290                 295                 300

Gln Asp Lys Ala Asn Pro Thr Ala Leu Leu Ser Ser Val Met Met
305                 310                 315                 320

Leu Asn His Met Gly Leu Thr Asn His Ala Asp Gln Ile Gln Asn Ala
                325                 330                 335

Val Leu Ser Thr Ile Ala Ser Gly Pro Glu Asn Arg Thr Gly Asp Leu
            340                 345                 350

Ala Gly Thr Ala Thr Thr Ser Ser Phe Thr Glu Ala Val Ile Lys Arg
        355                 360                 365

Leu

```
<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
tgcggccggc cgcagctttg cagag                                          25

<210> SEQ ID NO 4
<211> LENGTH: 30
<212> TYPE: DNA
<213> ORGANISM: Artificial Sequence
<220> FEATURE:
<223> OTHER INFORMATION: Synthetic DNA

<400> SEQUENCE: 4
tttgtttgtt tatgtgtgtt tattcgaaac                                     30

<210> SEQ ID NO 5
<211> LENGTH: 26
<212> TYPE: DNA
<213> ORGANISM: Artificial Sequence
<220> FEATURE:
<223> OTHER INFORMATION: Synthetic DNA

<400> SEQUENCE: 5
cttgacgggt attctgagca tcttac                                         26

<210> SEQ ID NO 6
<211> LENGTH: 35
<212> TYPE: DNA
<213> ORGANISM: Artificial Sequence
<220> FEATURE:
<223> OTHER INFORMATION: Synthetic DNA

<400> SEQUENCE: 6
tttgttttgt tgtttgtgt gatgaattta atttg                                35

<210> SEQ ID NO 7
<211> LENGTH: 35
<212> TYPE: DNA
<213> ORGANISM: Artificial Sequence
<220> FEATURE:
<223> OTHER INFORMATION: Synthetic DNA

<400> SEQUENCE: 7
aacaaacaaa acaaaatgct ttcactacgt caatc                               35

<210> SEQ ID NO 8
<211> LENGTH: 41
<212> TYPE: DNA
<213> ORGANISM: Artificial Sequence
<220> FEATURE:
<223> OTHER INFORMATION: Synthetic DNA

<400> SEQUENCE: 8
cttaatcttt gtcataagag catatctaga gctacacaaa g                        41

<210> SEQ ID NO 9
<211> LENGTH: 27
<212> TYPE: DNA
<213> ORGANISM: Artificial Sequence
<220> FEATURE:
<223> OTHER INFORMATION: Synthetic DNA
```

<400> SEQUENCE: 9
atgacaaaga ttaaggtagc taacccc                                          27

<210> SEQ ID NO 10
<211> LENGTH: 35
<212> TYPE: DNA
<213> ORGANISM: Artificial Sequence
<220> FEATURE:
<223> OTHER INFORMATION: Synthetic DNA

<400> SEQUENCE: 10
gaccaagtta gctggtatat cggtcctctg tgtag                                 35

<210> SEQ ID NO 11
<211> LENGTH: 21
<212> TYPE: DNA
<213> ORGANISM: Artificial Sequence
<220> FEATURE:
<223> OTHER INFORMATION: Synthetic DNA

<400> SEQUENCE: 11
ccagctaact tggtcgactt g                                                21

<210> SEQ ID NO 12
<211> LENGTH: 22
<212> TYPE: DNA
<213> ORGANISM: Artificial Sequence
<220> FEATURE:
<223> OTHER INFORMATION: Synthetic DNA

<400> SEQUENCE: 12
ttgcaaagaa ccgtcaccaa tg                                               22

<210> SEQ ID NO 13
<211> LENGTH: 38
<212> TYPE: DNA
<213> ORGANISM: Artificial Sequence
<220> FEATURE:
<223> OTHER INFORMATION: Synthetic DNA

<400> SEQUENCE: 13
acataaacaa acaaaatggc aaacccttttt tcgagatg                             38

<210> SEQ ID NO 14
<211> LENGTH: 37
<212> TYPE: DNA
<213> ORGANISM: Artificial Sequence
<220> FEATURE:
<223> OTHER INFORMATION: Synthetic DNA

<400> SEQUENCE: 14
agaatacccg tcaagctgga tagagcctca tcgttac                               37

<210> SEQ ID NO 15
<211> LENGTH: 41
<212> TYPE: DNA
<213> ORGANISM: Artificial Sequence
<220> FEATURE:
<223> OTHER INFORMATION: Synthetic DNA

<400> SEQUENCE: 15
aacaaacaaa acaaaatgac aaagattaag gtagctaacc c                          41

<210> SEQ ID NO 16
<211> LENGTH: 21
<212> TYPE: DNA
<213> ORGANISM: Artificial Sequence
<220> FEATURE:
<223> OTHER INFORMATION: Synthetic DNA

<400> SEQUENCE: 16
ccagctaact tggtcgactt g					21

<210> SEQ ID NO 17
<211> LENGTH: 33
<212> TYPE: DNA
<213> ORGANISM: Artificial Sequence
<220> FEATURE:
<223> OTHER INFORMATION: Synthetic DNA

<400> SEQUENCE: 17
cgtggctgcg agcgaagcca tcgcactgta cca					33

<210> SEQ ID NO 18
<211> LENGTH: 24
<212> TYPE: DNA
<213> ORGANISM: Artificial Sequence
<220> FEATURE:
<223> OTHER INFORMATION: Synthetic DNA

<400> SEQUENCE: 18
ctggatagag cctcatcgtt acac					24

<210> SEQ ID NO 19
<211> LENGTH: 41
<212> TYPE: DNA
<213> ORGANISM: Artificial Sequence
<220> FEATURE:
<223> OTHER INFORMATION: Synthetic DNA

<400> SEQUENCE: 19
acataaacaa acaaaatgct ttcactacgt caatctataa g					41

<210> SEQ ID NO 20
<211> LENGTH: 35
<212> TYPE: DNA
<213> ORGANISM: Artificial Sequence
<220> FEATURE:
<223> OTHER INFORMATION: Synthetic DNA

<400> SEQUENCE: 20
aatcactcct cattgtatat cggtcctctg tgtag					35

<210> SEQ ID NO 21
<211> LENGTH: 27
<212> TYPE: DNA
<213> ORGANISM: Artificial Sequence
<220> FEATURE:
<223> OTHER INFORMATION: Synthetic DNA

<400> SEQUENCE: 21
caatgaggag tgattttaca caaaaag					27

<210> SEQ ID NO 22
<211> LENGTH: 32
<212> TYPE: DNA
<213> ORGANISM: Artificial Sequence
<220> FEATURE:
<223> OTHER INFORMATION: Synthetic DNA

<400> SEQUENCE: 22
taataaaaga gcaacacagt ttatcttata tg                                32

<210> SEQ ID NO 23
<211> LENGTH: 50
<212> TYPE: DNA
<213> ORGANISM: Artificial Sequence
<220> FEATURE:
<223> OTHER INFORMATION: Synthetic DNA

<400> SEQUENCE: 23
acataaacaa acaaattta ttattagtct tttttttttt tgacaatatc                50

<210> SEQ ID NO 24
<211> LENGTH: 18
<212> TYPE: DNA
<213> ORGANISM: Artificial Sequence
<220> FEATURE:
<223> OTHER INFORMATION: Synthetic DNA

<400> SEQUENCE: 24
tcgctcgcag ccacgggt                                                 18

<210> SEQ ID NO 25
<211> LENGTH: 34
<212> TYPE: DNA
<213> ORGANISM: Artificial Sequence
<220> FEATURE:
<223> OTHER INFORMATION: Synthetic DNA

<400> SEQUENCE: 25
gttgctcttt tattattagt ctttttttt tttg                                34

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
cggtagcgct cattctgatg                                               20

<210> SEQ ID NO 27
<211> LENGTH: 21
<212> TYPE: DNA
<213> ORGANISM: Artificial Sequence
<220> FEATURE:
<223> OTHER INFORMATION: Synthetic DNA

<400> SEQUENCE: 27
tcaagcaaaa tgggagggta g                                             21

<210> SEQ ID NO 28
<211> LENGTH: 37
<212> TYPE: DNA
<213> ORGANISM: Artificial Sequence
<220> FEATURE:
<223> OTHER INFORMATION: Synthetic DNA

<400> SEQUENCE: 28
taacattcaa cgctattttc tcttacaatt atggagg                            37

<210> SEQ ID NO 29
<211> LENGTH: 42
<212> TYPE: DNA
<213> ORGANISM: Artificial Sequence
<220> FEATURE:
<223> OTHER INFORMATION: Synthetic DNA

<400> SEQUENCE: 29
tgaggctcta tccagtgaaa acaattcccc ttttttttgt tc                          42

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA

<400> SEQUENCE: 30
aagcctccac tgccatcact                                                   20

<210> SEQ ID NO 31
<211> LENGTH: 28
<212> TYPE: DNA
<213> ORGANISM: Artificial Sequence
<220> FEATURE:
<223> OTHER INFORMATION: Synthetic DNA

<400> SEQUENCE: 31
aaaaccacta agtgacaaag aactacgc                                          28

<210> SEQ ID NO 32
<211> LENGTH: 32
<212> TYPE: DNA
<213> ORGANISM: Artificial Sequence
<220> FEATURE:
<223> OTHER INFORMATION: Synthetic DNA

<400> SEQUENCE: 32
tcacttagtg gttttgatcc tctagagtcg ac                                     32

<210> SEQ ID NO 33
<211> LENGTH: 33
<212> TYPE: DNA
<213> ORGANISM: Artificial Sequence
<220> FEATURE:
<223> OTHER INFORMATION: Synthetic DNA

<400> SEQUENCE: 33
tggcagtgga ggcttgatcc ccgggtaccg agc                                    33

<210> SEQ ID NO 34
<211> LENGTH: 40
<212> TYPE: DNA
<213> ORGANISM: Artificial Sequence
<220> FEATURE:
<223> OTHER INFORMATION: Synthetic DNA

<400> SEQUENCE: 34
ggggcctgtc ttaagagaaa gagaggaaag gacttactac                             40

<210> SEQ ID NO 35
<211> LENGTH: 32
<212> TYPE: DNA
<213> ORGANISM: Artificial Sequence
<220> FEATURE:
<223> OTHER INFORMATION: Synthetic DNA

<400> SEQUENCE: 35
ggttaaagat tagcttctaa tattttaggt gg                           32

<210> SEQ ID NO 36
<211> LENGTH: 37
<212> TYPE: DNA
<213> ORGANISM: Artificial Sequence
<220> FEATURE:
<223> OTHER INFORMATION: Synthetic DNA

<400> SEQUENCE: 36
gctatggtgt gtgggctgca ggaattcgat atcaagc                      37

<210> SEQ ID NO 37
<211> LENGTH: 24
<212> TYPE: DNA
<213> ORGANISM: Artificial Sequence
<220> FEATURE:
<223> OTHER INFORMATION: Synthetic DNA

<400> SEQUENCE: 37
cccacacacc atagcttcaa aatg                                    24

<210> SEQ ID NO 38
<211> LENGTH: 29
<212> TYPE: DNA
<213> ORGANISM: Artificial Sequence
<220> FEATURE:
<223> OTHER INFORMATION: Synthetic DNA

<400> SEQUENCE: 38
tagattgcta tgctttcttt ctaatgagc                               29

<210> SEQ ID NO 39
<211> LENGTH: 44
<212> TYPE: DNA
<213> ORGANISM: Artificial Sequence
<220> FEATURE:
<223> OTHER INFORMATION: Synthetic DNA

<400> SEQUENCE: 39
aagcatagca atctaatcta aagaatgtct attccagaaa ctca              44

<210> SEQ ID NO 40
<211> LENGTH: 42
<212> TYPE: DNA
<213> ORGANISM: Artificial Sequence
<220> FEATURE:
<223> OTHER INFORMATION: Synthetic DNA

<400> SEQUENCE: 40
agctaatctt taacccttat ttagaagtgt caacaacgta tc                42

<210> SEQ ID NO 41
<211> LENGTH: 42
<212> TYPE: DNA
<213> ORGANISM: Artificial Sequence
<220> FEATURE:
<223> OTHER INFORMATION: Synthetic DNA

<400> SEQUENCE: 41
ctgcggccgg ccgcacttat ttagaagtgt caacaacgta tc                42

<210> SEQ ID NO 42
<211> LENGTH: 25
<212> TYPE: DNA
<213> ORGANISM: Artificial Sequence
<220> FEATURE:
<223> OTHER INFORMATION: Synthetic DNA

<400> SEQUENCE: 42
tgcggccggc cgcagctttg cagag                                    25

<210> SEQ ID NO 43
<211> LENGTH: 18
<212> TYPE: DNA
<213> ORGANISM: Artificial Sequence
<220> FEATURE:
<223> OTHER INFORMATION: Synthetic DNA

<400> SEQUENCE: 43
agagcgcgcc tcgttcag                                            18

<210> SEQ ID NO 44
<211> LENGTH: 35
<212> TYPE: DNA
<213> ORGANISM: Artificial Sequence
<220> FEATURE:
<223> OTHER INFORMATION: Synthetic DNA

<400> SEQUENCE: 44
aacgaggcgc gctctacgac atcgtcgaat atgat                         35

<210> SEQ ID NO 45
<211> LENGTH: 33
<212> TYPE: DNA
<213> ORGANISM: Artificial Sequence
<220> FEATURE:
<223> OTHER INFORMATION: Synthetic DNA

<400> SEQUENCE: 45
tattaattta gtgtgtgtat ttgtgtttgt gtg                           33

<210> SEQ ID NO 46
<211> LENGTH: 34
<212> TYPE: DNA
<213> ORGANISM: Artificial Sequence
<220> FEATURE:
<223> OTHER INFORMATION: Synthetic DNA

<400> SEQUENCE: 46
cacactaaat taataatgag ccatattcaa cggg                          34

<210> SEQ ID NO 47
<211> LENGTH: 38
<212> TYPE: DNA
<213> ORGANISM: Artificial Sequence
<220> FEATURE:
<223> OTHER INFORMATION: Synthetic DNA

<400> SEQUENCE: 47
agctaatctt taaccttaca accaattaac caattctg                      38

<210> SEQ ID NO 48
<211> LENGTH: 38
<212> TYPE: DNA
<213> ORGANISM: Artificial Sequence
<220> FEATURE:
<223> OTHER INFORMATION: Synthetic DNA

<400> SEQUENCE: 48
tttagtagac atgcattaca accaattaac caattctg                        38

<210> SEQ ID NO 49
<211> LENGTH: 37
<212> TYPE: DNA
<213> ORGANISM: Artificial Sequence
<220> FEATURE:
<223> OTHER INFORMATION: Synthetic DNA

<400> SEQUENCE: 49
tgcatgtcta ctaaactcac aaattagagc ttcaatt                         37

<210> SEQ ID NO 50
<211> LENGTH: 48
<212> TYPE: DNA
<213> ORGANISM: Artificial Sequence
<220> FEATURE:
<223> OTHER INFORMATION: Synthetic DNA

<400> SEQUENCE: 50
gctcagaata cccgtcaagg ggtaataact gatataatta aattgaag             48

<210> SEQ ID NO 51
<211> LENGTH: 39
<212> TYPE: DNA
<213> ORGANISM: Artificial Sequence
<220> FEATURE:
<223> OTHER INFORMATION: Synthetic DNA

<400> SEQUENCE: 51
aacaaacaaa acaaaatggc aaagaagctc aacaagtac                      39

<210> SEQ ID NO 52
<211> LENGTH: 41
<212> TYPE: DNA
<213> ORGANISM: Artificial Sequence
<220> FEATURE:
<223> OTHER INFORMATION: Synthetic DNA

<400> SEQUENCE: 52
agctaatctt taaccatttc gtagattata attaaggcga c                   41

<210> SEQ ID NO 53
<211> LENGTH: 31
<212> TYPE: DNA
<213> ORGANISM: Artificial Sequence
<220> FEATURE:
<223> OTHER INFORMATION: Synthetic DNA

<400> SEQUENCE: 53
atttcgtaga ttataattaa ggcgactttt c                              31

<210> SEQ ID NO 54
<211> LENGTH: 44
<212> TYPE: DNA
<213> ORGANISM: Artificial Sequence
<220> FEATURE:
<223> OTHER INFORMATION: Synthetic DNA

<400> SEQUENCE: 54
cacggtggaa gaaggggtta aagattagct tctaatattt tagg                44

<210> SEQ ID NO 55
<211> LENGTH: 35
<212> TYPE: DNA
<213> ORGANISM: Artificial Sequence
<220> FEATURE:
<223> OTHER INFORMATION: Synthetic DNA

<400> SEQUENCE: 55
tataatctac gaaattaata agaaaggtga ccgtg                    35

<210> SEQ ID NO 56
<211> LENGTH: 36
<212> TYPE: DNA
<213> ORGANISM: Artificial Sequence
<220> FEATURE:
<223> OTHER INFORMATION: Synthetic DNA

<400> SEQUENCE: 56
gtcaaatcaa tcaaaatggc aacaagacct cccttg                   36

<210> SEQ ID NO 57
<211> LENGTH: 28
<212> TYPE: DNA
<213> ORGANISM: Artificial Sequence
<220> FEATURE:
<223> OTHER INFORMATION: Synthetic DNA

<400> SEQUENCE: 57
tttgattgat ttgactgtgt tattttgc                            28

<210> SEQ ID NO 58
<211> LENGTH: 21
<212> TYPE: DNA
<213> ORGANISM: Artificial Sequence
<220> FEATURE:
<223> OTHER INFORMATION: Synthetic DNA

<400> SEQUENCE: 58
ccttcttcca ccgtgtcaag c                                   21

<210> SEQ ID NO 59
<211> LENGTH: 34
<212> TYPE: DNA
<213> ORGANISM: Artificial Sequence
<220> FEATURE:
<223> OTHER INFORMATION: Synthetic DNA

<400> SEQUENCE: 59
agaaagagag gaaaggactt actacagtat attg                     34

<210> SEQ ID NO 60
<211> LENGTH: 38
<212> TYPE: DNA
<213> ORGANISM: Artificial Sequence
<220> FEATURE:
<223> OTHER INFORMATION: Synthetic DNA

<400> SEQUENCE: 60
ctttcctctc tttctctatt ttcgaggacc ttgtcacc                 38

<210> SEQ ID NO 61
<211> LENGTH: 45
<212> TYPE: DNA
<213> ORGANISM: Artificial Sequence
<220> FEATURE:
<223> OTHER INFORMATION: Synthetic DNA

<400> SEQUENCE: 61
acgggcagct ggcatttgt ttgtttatgt gtgtttattc gaaac                45

<210> SEQ ID NO 62
<211> LENGTH: 18
<212> TYPE: DNA
<213> ORGANISM: Artificial Sequence
<220> FEATURE:
<223> OTHER INFORMATION: Synthetic DNA

<400> SEQUENCE: 62
atgccagctg cccgtttc                                             18

<210> SEQ ID NO 63
<211> LENGTH: 38
<212> TYPE: DNA
<213> ORGANISM: Artificial Sequence
<220> FEATURE:
<223> OTHER INFORMATION: Synthetic DNA

<400> SEQUENCE: 63
aaccgcttta tagaatatgt acacgtatat gtgacgag                       38

<210> SEQ ID NO 64
<211> LENGTH: 29
<212> TYPE: DNA
<213> ORGANISM: Artificial Sequence
<220> FEATURE:
<223> OTHER INFORMATION: Synthetic DNA

<400> SEQUENCE: 64
ttctataaag cggttaaatt cgtattggc                                 29

<210> SEQ ID NO 65
<211> LENGTH: 33
<212> TYPE: DNA
<213> ORGANISM: Artificial Sequence
<220> FEATURE:
<223> OTHER INFORMATION: Synthetic DNA

<400> SEQUENCE: 65
agctaatctt taaccatgcc agagcctgct cca                            33

<210> SEQ ID NO 66
<211> LENGTH: 33
<212> TYPE: DNA
<213> ORGANISM: Artificial Sequence
<220> FEATURE:
<223> OTHER INFORMATION: Synthetic DNA

<400> SEQUENCE: 66
taatacatat tcaaaatgcc agagcctgct cca                            33

<210> SEQ ID NO 67
<211> LENGTH: 37
<212> TYPE: DNA
<213> ORGANISM: Artificial Sequence
<220> FEATURE:
<223> OTHER INFORMATION: Synthetic DNA

<400> SEQUENCE: 67
tttgaatatg tattacttgg ttatggttat atatgac                        37

<210> SEQ ID NO 68
<211> LENGTH: 25
<212> TYPE: DNA
<213> ORGANISM: Artificial Sequence
<220> FEATURE:
<223> OTHER INFORMATION: Synthetic DNA

<400> SEQUENCE: 68
actggtagag agcgactttg tatgc                                  25

<210> SEQ ID NO 69
<211> LENGTH: 41
<212> TYPE: DNA
<213> ORGANISM: Artificial Sequence
<220> FEATURE:
<223> OTHER INFORMATION: Synthetic DNA

<400> SEQUENCE: 69
caaagtcgct ctctaccagt cgctttcaat tcatttgggt g                41

<210> SEQ ID NO 70
<211> LENGTH: 26
<212> TYPE: DNA
<213> ORGANISM: Artificial Sequence
<220> FEATURE:
<223> OTHER INFORMATION: Synthetic DNA

<400> SEQUENCE: 70
ggtgccattg tatatgagat agttga                                 26

<210> SEQ ID NO 71
<211> LENGTH: 25
<212> TYPE: DNA
<213> ORGANISM: Artificial Sequence
<220> FEATURE:
<223> OTHER INFORMATION: Synthetic DNA

<400> SEQUENCE: 71
atatacaatg gcacctgtta caatt                                  25

<210> SEQ ID NO 72
<211> LENGTH: 41
<212> TYPE: DNA
<213> ORGANISM: Artificial Sequence
<220> FEATURE:
<223> OTHER INFORMATION: Synthetic DNA

<400> SEQUENCE: 72
agctaatctt taaccctatt ttttatttct tttaagtgcc g                41

<210> SEQ ID NO 73
<211> LENGTH: 39
<212> TYPE: DNA
<213> ORGANISM: Artificial Sequence
<220> FEATURE:
<223> OTHER INFORMATION: Synthetic DNA

<400> SEQUENCE: 73
ggggcctgtc ttaagctatt ttttatttct tttaagtgc                   39

<210> SEQ ID NO 74
<211> LENGTH: 46
<212> TYPE: DNA
<213> ORGANISM: Artificial Sequence
<220> FEATURE:
<223> OTHER INFORMATION: Synthetic DNA

<400> SEQUENCE: 74
aatctaatct aaagaggtta aagattagct tctaatattt taggtg        46

<210> SEQ ID NO 75
<211> LENGTH: 25
<212> TYPE: DNA
<213> ORGANISM: Artificial Sequence
<220> FEATURE:
<223> OTHER INFORMATION: Synthetic DNA

<400> SEQUENCE: 75
cttaagacag gcccctttc ctttg        25

<210> SEQ ID NO 76
<211> LENGTH: 41
<212> TYPE: DNA
<213> ORGANISM: Artificial Sequence
<220> FEATURE:
<223> OTHER INFORMATION: Synthetic DNA

<400> SEQUENCE: 76
tctttagatt agattgctat gctttctttc taatgagcaa g        41

<210> SEQ ID NO 77
<211> LENGTH: 20
<212> TYPE: DNA
<213> ORGANISM: Artificial Sequence
<220> FEATURE:
<223> OTHER INFORMATION: Synthetic DNA

<400> SEQUENCE: 77
gttgaagtcg cctggtagcc        20

<210> SEQ ID NO 78
<211> LENGTH: 20
<212> TYPE: DNA
<213> ORGANISM: Artificial Sequence
<220> FEATURE:
<223> OTHER INFORMATION: Synthetic DNA

<400> SEQUENCE: 78
cggtgatccc cttgaaaaag        20

<210> SEQ ID NO 79
<211> LENGTH: 16
<212> TYPE: DNA
<213> ORGANISM: Artificial Sequence
<220> FEATURE:
<223> OTHER INFORMATION: Synthetic DNA

<400> SEQUENCE: 79
tgcggccggc cgcagc        16

<210> SEQ ID NO 80
<211> LENGTH: 34
<212> TYPE: DNA
<213> ORGANISM: Artificial Sequence
<220> FEATURE:
<223> OTHER INFORMATION: Synthetic DNA

<400> SEQUENCE: 80
cgctaacatt caacgctaag agcgcgcctc gttc        34

<210> SEQ ID NO 81
<211> LENGTH: 26
<212> TYPE: DNA
<213> ORGANISM: Artificial Sequence
<220> FEATURE:
<223> OTHER INFORMATION: Synthetic DNA

<400> SEQUENCE: 81
tagcgttgaa tgttagcgtc aacaac                                    26

<210> SEQ ID NO 82
<211> LENGTH: 30
<212> TYPE: DNA
<213> ORGANISM: Artificial Sequence
<220> FEATURE:
<223> OTHER INFORMATION: Synthetic DNA

<400> SEQUENCE: 82
tttgtttgtt tatgtgtgtt tattcgaaac                                30

<210> SEQ ID NO 83
<211> LENGTH: 37
<212> TYPE: DNA
<213> ORGANISM: Artificial Sequence
<220> FEATURE:
<223> OTHER INFORMATION: Synthetic DNA

<400> SEQUENCE: 83
tgcatgtcta ctaaactcac aaattagagc ttcaatt                        37

<210> SEQ ID NO 84
<211> LENGTH: 41
<212> TYPE: DNA
<213> ORGANISM: Artificial Sequence
<220> FEATURE:
<223> OTHER INFORMATION: Synthetic DNA

<400> SEQUENCE: 84
gtcgaccaag ttagctgggg gtaataactg atataattaa a                   41

<210> SEQ ID NO 85
<211> LENGTH: 33
<212> TYPE: DNA
<213> ORGANISM: Artificial Sequence
<220> FEATURE:
<223> OTHER INFORMATION: Synthetic DNA

<400> SEQUENCE: 85
acataaacaa acaaaatgac cgaccaagcg acg                            33

<210> SEQ ID NO 86
<211> LENGTH: 35
<212> TYPE: DNA
<213> ORGANISM: Artificial Sequence
<220> FEATURE:
<223> OTHER INFORMATION: Synthetic DNA

<400> SEQUENCE: 86
agtttagtag acatgcatca tgagatgcct gcaag                          35

<210> SEQ ID NO 87
<211> LENGTH: 36
<212> TYPE: DNA
<213> ORGANISM: Artificial Sequence
<220> FEATURE:
<223> OTHER INFORMATION: Synthetic DNA

```
<400> SEQUENCE: 87
ctgcggccgg ccgcacttcc aagcatctca taaacc                              36

<210> SEQ ID NO 88
<211> LENGTH: 34
<212> TYPE: DNA
<213> ORGANISM: Artificial Sequence
<220> FEATURE:
<223> OTHER INFORMATION: Synthetic DNA

<400> SEQUENCE: 88
acataaacaa acaaagatgt acgatcgcct gcac                                34

<210> SEQ ID NO 89
<211> LENGTH: 34
<212> TYPE: DNA
<213> ORGANISM: Artificial Sequence
<220> FEATURE:
<223> OTHER INFORMATION: Synthetic DNA

<400> SEQUENCE: 89
gacggttctt tgcaagatgt acgatcgcct gcac                                34
```

METHOD FOR PRODUCING ISOBUTANOL AND RECOMBINANT MICROORGANISM CAPABLE OF PRODUCING ISOBUTANOL

CROSS REFERENCE TO RELATED APPLICATIONS

This application is a National Stage of International Application No. PCT/JP2012/006764filed Oct. 23, 2012, claiming priority based on Japanese Patent Application No. 2011-233268, filed Oct. 24, 2011, the contents of all of which are incorporated herein by reference in their entirety.

TECHNICAL FIELD

The present invention relates to a method for producing isobutanol utilizing recombinant microorganisms comprising genes associated with biosynthesis of isobutanol (2-methylpropan-1-ol) and capable of producing isobutanol and recombinant microorganisms.

BACKGROUND ART

Isobutanol is also referred to as 2-methylpropan-1-ol or 2-methylpropyl alcohol, and it is extensively utilized in the chemical engineering field. Isobutanol has heretofore been produced via a so-called fermentation process. For example, Patent Document 1 discloses a recombinant microorganism prepared by substituting at least one of the genes associated with the isobutanol biosynthesis pathway with a gene originating from an organism other than the host microorganism and a method for producing isobutanol utilizing such recombinant microorganism. Genes introduced into host microorganisms are the acetolactate synthase gene, the acetohydroxy acid reductoisomerase gene, the acetohydroxy acid dehydratase gene, the branched chain keto acid decarboxylase gene, and the branched chain alcohol dehydrogenase gene. Examples of host microorganisms that are employed include *Escherichia coli*, *Bacillus subtilis*, *Saccharomyces cerevisiae*, and *Lactobacillus plantarum*.

Patent Document 2 discloses a recombinant microorganism with a metabolic pathway modified so as to be capable of producing an alcohol having 3 to 5 carbon atoms. Patent Document 2 also discloses the introduction of a mutant ketol acid reductoisomerase gene resulting from an increase in NADH dependence or modification of coenzyme specificity from NADPH specificity to NADP specificity into such recombinant microorganism. Further, Patent Document 3 discloses a mutant ketol acid reductoisomerase gene capable of binding to NADH. Techniques of both Patent Documents 2 and 3 are intended to increase NADPH and to decrease NADH in the isobutanol biosynthesis pathway, thereby improving the isobutanol yield.

None of Patent Documents 1 to 3 are sufficient in terms of the isobutanol yield, and further improvement in the isobutanol yield has been desired in the production of isobutanol via a fermentation process.

CITATION LIST

Patent Literature

PTL 1: JP Patent Publication (Kokai) No. 2009-513136 A
PTL 2: WO 2010/051527
PTL 3: WO 2009/085953

SUMMARY OF INVENTION

Technical Problem

Under the above circumstances, it is an object of the present invention to provide a method for producing isobutanol with excellent productivity via a fermentation process. It is another object to provide a recombinant microorganism having excellent isobutanol productivity.

Solution to Problem

The present inventors have conducted concentrated studies in order to attain the above objects. As a result, they discovered that the amount of isobutanol produced would be significantly increased by utilizing a reaction such that a NADP-dependent isocitrate dehydrogenase generates NADPH from NADP as an NADPH source for the reaction of converting 2-acetolactate into 2,3-dihydroxy-isovalerate in the isobutanol biosynthesis pathway. This has led to the completion of the present invention.

The present invention is as follows.

(1) A method for producing isobutanol comprising steps of: culturing a recombinant yeast strain comprising the isobutanol biosynthesis pathway, in which expression of the NADP-dependent isocitrate dehydrogenase gene is reinforced; and obtaining isobutanol from the culture.

(2) The method for producing isobutanol according to (1), wherein the recombinant yeast strains result from reinforcement of the NADP-dependent isocitrate dehydrogenase gene expression in the intracellular tissue in which acetohydroxy acid reductoisomerase that catalyzes a reaction of converting 2-acetolactate into 2,3-dihydroxy-isovalerate using an NADPH as a coenzyme in the isobutanol biosynthesis pathway functions.

(3) The method for producing isobutanol according to (2), wherein the intracellular tissue is mitochondria.

(4) The method for producing isobutanol according to (3), wherein the NADP-dependent isocitrate dehydrogenase gene comprises a region encoding a mitochondrial transport signal or is a fusion gene to which said region is added.

(5) The method for producing isobutanol according to (2), wherein the recombinant yeast strain comprises genes encoding enzymes involving the pathway from pyruvate to 2-keto-isovalerate in the isobutanol biosynthesis pathway expressed in the cytoplasm.

(6) The method for producing isobutanol according to (2), wherein the recombinant yeast strain lacks the NAD-dependent isocitrate dehydrogenase gene that functions in the intracellular tissue.

(7) A recombinant yeast strain comprising the isobutanol biosynthesis pathway, in which the expression of the NADP-dependent isocitrate dehydrogenase gene is reinforced in the intracellular tissue in which acetohydroxy acid reductoisomerase that catalyzes a reaction of converting 2-acetolactate into 2,3-dihydroxy-isovalerate using an NADPH as a coenzyme functions.

(8) The recombinant yeast strain according to (7), wherein the intracellular tissue is mitochondria.

(9) The recombinant yeast strain according to (8), wherein the NADP-dependent isocitrate dehydrogenase gene comprises a region encoding a mitochondrial transport signal or is a fusion gene to which such region is added.

(10) The recombinant yeast strain according to (7), wherein the genes encoding enzymes involving the pathway from pyruvate to 2-keto-isovalerate in the isobutanol biosynthesis pathway are expressed in the cytoplasm.

(11) The recombinant yeast strain according to (7), which lacks the NAD-dependent isocitrate dehydrogenase gene that functions in the intracellular tissue.

This description contains part or all of the contents as disclosed in the description and/or drawings of Japanese Patent Application No. 2011-233268, based on which the present application claims priority.

Advantageous Effects of Invention

The present invention can provide a method for producing isobutanol that yields excellent productivity using recombinant microorganisms exerting a significantly improved capacity for isobutanol production. According to the method for producing isobutanol of the present invention, specifically, productivity when producing isobutanol, which has been extensively utilized in the chemical engineering field, can be improved, and the isobutanol production cost can be reduced.

The recombinant microorganism according to the present invention has superior capacity for isobutanol production compared with existing recombinant microorganisms capable of producing isobutanol.

DESCRIPTION OF EMBODIMENTS

Hereafter, the present invention is described in detail.

The method for producing isobutanol according to the present invention comprises culturing recombinant microorganisms, which is obtained by reinforcing expression of the NADP-dependent isocitrate dehydrogenase gene in a yeast strain capable of producing isobutanol and obtaining isobutanol from the culture product.

Figure 1:
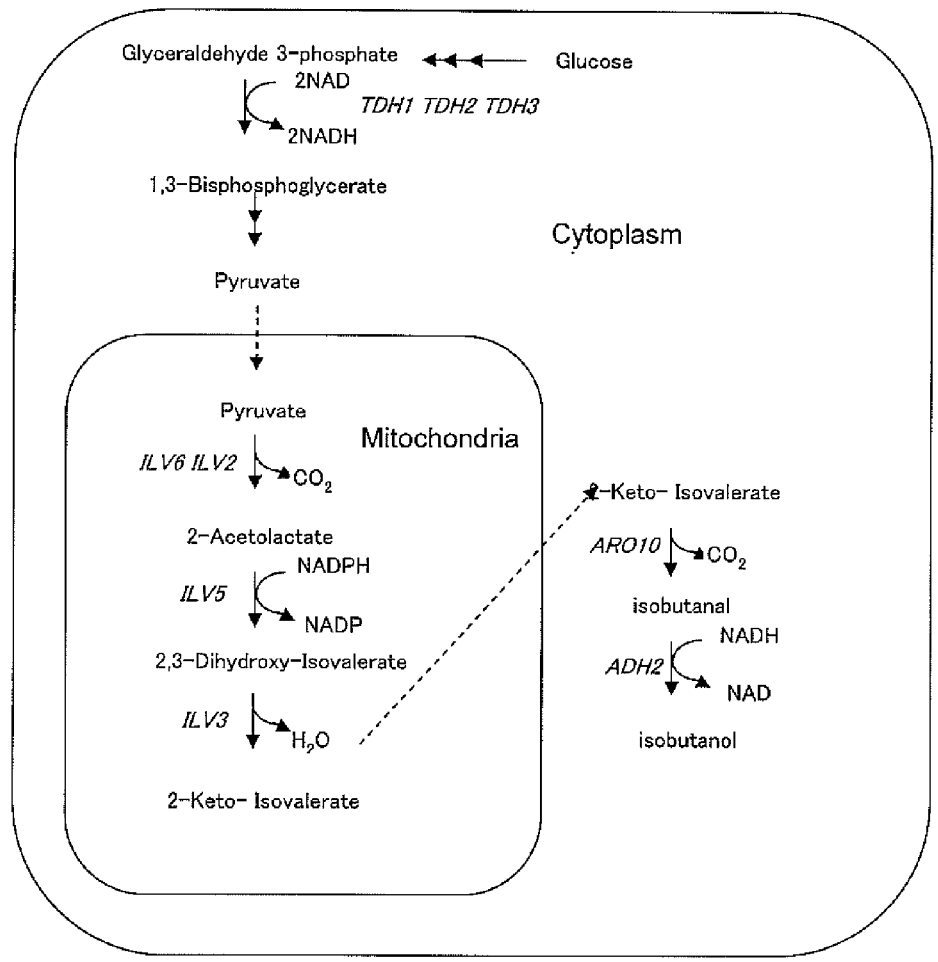
FIG. 1 schematically shows a configuration of a principal part of a biosynthesis pathway from glucose to isobutanol.

The isobutanol biosynthesis pathway is described. As shown in FIG. 1, glucose is metabolized into pyruvate by the glycolysis system in the cytoplasm. In this process, glyceraldehyde-3-phosphate dehydrogenase (TDH1 to TDH3) is associated with the reaction for converting glyceraldehyde-3-phosphate into 1,3-bisphosphoglycerate. In the metabolic reaction conducted by the glyceraldehyde-3-phosphate dehydrogenase, two nicotinamide adenine dinucleotide (NAD) molecules are converted into two reduced nicotinamide adenine dinucleotide (NADH) molecules.

Pyruvate biosynthesized by the glycolysis system in the cytoplasm is transported to the mitochondria, used as a substrate of acetolactate synthase (ILV2, ILV6) in the mitochondria, and converted into 2-acetolactate. 2-Acetolactate is used as a substrate of acetohydroxy acid reductoisomerase (ILV5) in the mitochondria and is converted into 2,3-hydroxy-isovalerate. 2,3-Hydroxy-isovalerate is used as a substrate of dihydroxy acid dehydratase (ILV3) in the mitochondria and is converted into 2-keto-isovalerate. In the mitochondrial metabolic pathway, a single reduced nicotinamide adenine dinucleotide phosphate (NADPH) molecule is converted into a single nicotinamide adenine dinucleotide phosphate (NADP) molecule in the metabolic reaction conducted by acetohydroxy acid reductoisomerase (ILV5).

2-Keto-isovalerate biosynthesized in the mitochondria is transported to the cytoplasm, used as a substrate of 2-ketoacid decarboxylase (ARO10) in the cytoplasm, and then converted into isobutanal. Isobutanal is used as a substrate of alcohol dehydrogenase in the cytoplasm and then converted into isobutanol. In the metabolic reaction conducted by alcohol dehydrogenase in the metabolic pathway in the cytoplasm, a single NADH molecule is converted into a single NAD molecule.

As described above, NADH increases and NADPH decreases when a single isobutanol molecule is biosynthesized from a single glucose molecule in the metabolic pathway from glucose to isobutanol.

The method for producing isobutanol of the present invention involves the use of a recombinant yeast strain prepared by modifying a yeast strain having an isobutanol biosynthesis pathway so as to reinforce expression of the NADP-dependent isocitrate dehydrogenase gene. The recombinant yeast strain modified so as to reinforce expression of the NADP-dependent isocitrate dehydrogenase gene can use NADPH generated by the NADP-dependent isocitrate dehydrogenase as a source of NADPH for the reaction for converting 2-acetolactate into 2,3-dihydroxy-isovalerate in the isobutanol biosynthesis pathway. This can prevent the lowering in isobutanol productivity resulting from depletion or lack of NADPH in the isobutanol biosynthesis pathway in the recombinant yeast strain. Thus, isobutanol productivity can be maintained.

The term "yeast strain comprising the isobutanol biosynthesis pathway" used herein refers to a yeast strain that naturally comprises the isobutanol biosynthesis pathway or a recombinant microorganism that is modified to have the isobutanol biosynthesis pathway. In addition, a recombinant microorganism that is modified to allow some or all reactions, which are conducted in the mitochondria (i.e., conversion from pyruvate into 2-keto-isovalerate), to proceed in the cytoplasm in the isobutanol biosynthesis pathway is within the scope of the recombinant yeast strain. In such a case, a yeast strain may be modified so as to proceed the reaction in the cytoplasm while maintaining the metabolic pathway in the mitochondria. Alternatively, a yeast strain may be modified so as to allow the reactions to proceed in the cytoplasm instead of the metabolic pathway in the mitochondria.

Expression of the NADP-dependent isocitrate dehydrogenase genes may be reinforced by any conventional techniques, such as a method of integrating plural copies of such genes into the chromosome or a method of ligating the genes to promoters for high-level expression and integrating a single copy of the genes or plural copies of the genes into the chromosome. Expression of the NADP-dependent isocitrate dehydrogenase genes may be reinforced by a method involving substituting the promoters of the NADP-dependent isocitrate dehydrogenase genes inherent to a host yeast strain (the host may be a wild-type or recombinant yeast strain) with promoters for high-level expression. Reinforced expression of the NADP-dependent isocitrate dehydrogenase genes means reinforced enzyme activity of NADP-dependent isocitrate dehydrogenase, in other words. Thus, a method for reinforcing expression of the NADP-dependent isocitrate dehydrogenase genes includes a method for reinforcing enzyme activity of NADP-dependent isocitrate dehydrogenase. Further, expression of the NADP-dependent isocitrate dehydrogenase genes may be reinforced by performing the above-described methods in adequate combinations.

When the acetohydroxy acid reductoisomerase reaction in the isobutanol biosynthesis pathway is allowed to proceed in the mitochondria, in particular, it is preferable that expression of the NADP-dependent isocitrate dehydrogenase genes be reinforced in the mitochondria. When the acetohydroxy acid reductoisomerase reaction in the isobutanol biosynthesis pathway is allowed to proceed in the cytoplasm, it is preferable that expression of the NADP-dependent isocitrate dehydrogenase genes be reinforced in the cytoplasm.

Some types of NADP-dependent isocitrate dehydrogenase genes are naturally expressed in the mitochondria, and other types thereof are expressed in the cytoplasm. When expression of the NADP-dependent isocitrate dehydrogenase genes is to be reinforced in the mitochondria as described above, expression of the genes that are naturally expressed in the mitochondria may be reinforced, or the genes that are naturally expressed in the cytoplasm may be modified so as to be expressed in the mitochondria. In the latter case, an oligonucleotide encoding the mitochondrial transport signal may be fused to a gene that is naturally expressed in the cytoplasm, and the resulting fusion gene may be expressed. When expression of the NADP-dependent isocitrate dehydrogenase gene is reinforced in the cytoplasm as described above, expression of the gene that is naturally expressed in the cytoplasm may be reinforced. Alternatively, a gene that is naturally expressed in the mitochondria may be modified to express a mutant gene lacking a region encoding the mitochondrial transport signal.

In any case, it is preferable that expression of NADP-dependent isocitrate dehydrogenase be reinforced, in such a manner that a reaction of biosynthesizing NADPH with the aid of NADP-dependent isocitrate dehydrogenase is allowed to proceed in the intracellular tissue (i.e., the mitochondria and/or cytoplasm) where the reaction mediated by the acetohydroxy acid reductoisomerase is allowed to proceed. Thus, NADPH that is necessary for the acetohydroxy acid reductoisomerase reaction (from 2-acetolactate to 2,3-dihydroxyisovalerate) can be supplied, and lowered isobutanol productivity resulting from depletion or reduction in NADPH can be prevented.

<NADP-Dependent Isocitrate Dehydrogenase>

Figure 2:
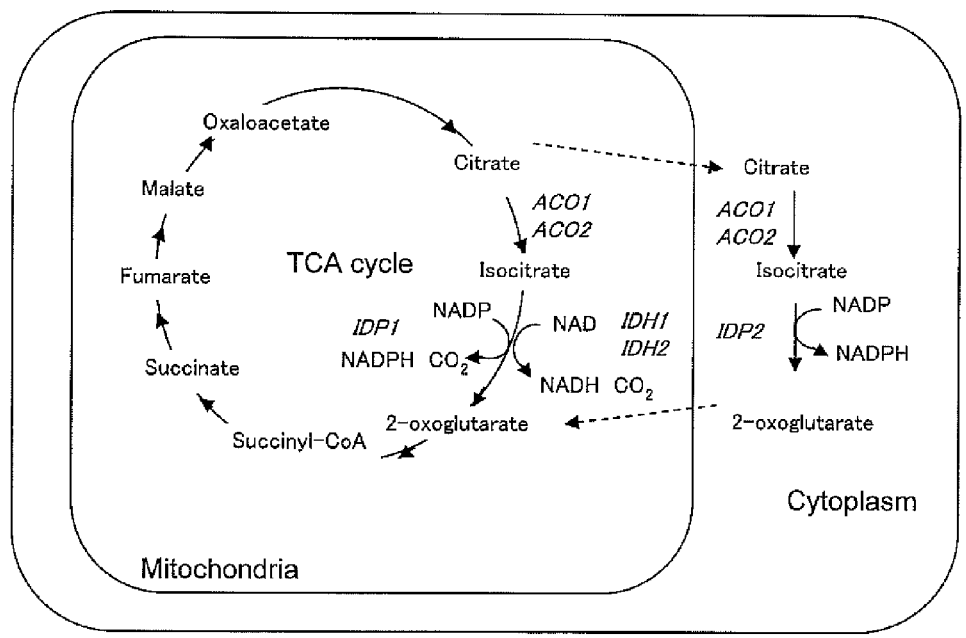
FIG. 2 schematically shows a configuration of a principal part of a citric acid cycle.

Hereafter, NADP-dependent isocitrate dehydrogenase is described in detail. The NADP-dependent isocitrate dehydrogenase is an enzyme that catalyzes a reaction for generating 2-oxoglutarate using isocitrate as a substrate and requires NADP as a coenzyme. This enzyme constitutes a citric acid cycle (see FIG. 2). Also, the NAD-dependent isocitrate dehydrogenase that requires NAD as a coenzyme is known. In the case of *Saccharomyces cerevisiae*, in particular, the IPD1 gene and the IPD2 gene are known as the NADP-dependent isocitrate dehydrogenase genes, as shown in FIG. 2. The IPD1 gene encodes NADP-dependent isocitrate dehydrogenase having a mitochondrial transport signal. The IPD2 gene encodes NADP-dependent isocitrate dehydrogenase having no mitochondrial transport signal. As the NAD-dependent isocitrate dehydrogenase genes of *Saccharomyces cerevisiae*, the IDH1 gene and the IDH2 gene that function in the mitochondria are known, as shown in FIG. 2.

When the NADP-dependent isocitrate dehydrogenase gene is introduced into a host yeast strain in an expressible manner in order to reinforce gene expression, in the present invention, the NADP-dependent isocitrate dehydrogenase gene is not particularly limited, and any known gene can be used. Specifically, the origin of the NADP-dependent isocitrate dehydrogenase gene to be introduced is not limited. The NADP-dependent isocitrate dehydrogenase genes originating from various organisms can be identified using, for example, the International Nucleotide Sequence Databases (DDBJ/EMBL/GenBank), and the nucleotide sequences of the genes and the amino acid sequences of proteins encoded thereby can further be identified. For example, SEQ ID NOs: 1 and 2 show the nucleotide sequence of the IPD2 gene, which is a NADP-dependent isocitrate dehydrogenase gene originating from *Saccharomyces cerevisiae*, and the amino acid sequence of the IPD2 protein, respectively.

When *Saccharomyces cerevisiae* is used as a host yeast strain, the NADP-dependent isocitrate dehydrogenase gene originating from *Saccharomyces cerevisiae* is preferably introduced. When *Saccharomyces cerevisiae* is used as a host yeast strain, in particular, the NADP-dependent isocitrate dehydrogenase gene introduced is preferably the IPD2 gene to which a region encoding the mitochondrial transport signal is fused. The IPD2 gene to which a region encoding the mitochondrial transport signal is fused can localize the NADP-dependent isocitrate dehydrogenase in the mitochondria that is naturally expressed in the cytoplasm and functions therein. Via introduction of such fusion gene, specifically, the NADP-dependent isocitrate dehydrogenase that naturally functions in the cytoplasm can be allowed to function in the mitochondria. Thus, such fusion gene is expressed in the mitochondria together with the IPD1 gene that is naturally expressed in the mitochondria. This can significantly improve the NADP-dependent isocitrate dehydrogenase activity in the mitochondria.

The IPD2 gene is not limited to a gene comprising the nucleotide sequence as shown in SEQ ID NO: 1 or a gene encoding a protein comprising the amino acid sequence as shown in SEQ ID NO: 2. The IPD2 gene may encode a protein comprising an amino acid sequence having a high degree of similarity (or identity) with the amino acid sequence as shown in SEQ ID NO: 2 and comprising NADP-dependent isocitrate dehydrogenase. In the present invention, a high degree of similarity (or identity) is, for example, 80% or higher consistency, preferably 90% or higher consistency, more preferably 95% or higher consistency, and most preferably 97% or higher consistency. Consistency is determined by aligning the amino acid sequence as shown in SEQ ID NO: 1 or 2 with another amino acid sequence using a program that search for sequence similarity (such program may be occasionally referred to as a "homology search program") and determining the percentage of amino acid residues in the other amino acid sequence that are consistent with the amino acid sequence as shown in SEQ ID NO: 1 or 2.

Alternatively, the IPD2 gene may be a gene encoding a protein comprising an amino acid sequence derived from the amino acid sequence as shown in SEQ ID NO: 2 by substitution, deletion, addition, or insertion of 1 or a plurality of amino acids and comprising NADP-dependent isocitrate dehydrogenase. The term "a plurality of amino acids" used herein refers to, for example, 2 to 30 amino acids, preferably 2 to 20 amino acids, more preferably 2 to 10 amino acids, and most preferably 2 to 5 amino acids.

The IPD2 gene may be a polynucleotide that hybridizes under stringent conditions to part or the entire polynucleotide comprising a nucleotide sequence complementary to the nucleotide sequence as shown in SEQ ID NO: 1 and encodes a protein having NADP-dependent isocitrate dehydrogenase. Hybridization under stringent conditions is carried out by maintaining coupling under washing conditions at 60 degrees C. in the presence of 2×SSC. Hybridization can be carried out via conventional techniques, such as the method described in J. Sambrook et al., Molecular Cloning: A Laboratory Manual, 2nd Ed., Cold Spring Harbor Laboratory, 1989.

The gene encoding a protein having an amino acid sequence that differs from the amino acid sequence as shown in SEQ ID NO: 2 can be isolated from a *Saccharomyces cerevisiae* strain that is different from, for example, a *Saccharomyces cerevisiae* strain having the IPD2 gene comprising the nucleotide sequence as shown in SEQ ID NO: 1. Alternatively, a polynucleotide comprising the nucleotide sequence as shown in SEQ ID NO: 1 may be modified in accordance with a technique known in the art in order to isolate the gene of interest. Mutation can be introduced into a nucleotide sequence via known techniques, such as the Kunkel method or the Gapped duplex method, or techniques in accordance therewith. For example, a mutagenesis kit utilizing site-directed mutagenesis (e.g., Mutant-K or Mutant-G: tradename; Takara) or the LA PCR in vitro Mutagenesis Series kit (tradename, Takara) may be used to introduce mutation.

The NADP-dependent isocitrate dehydrogenase activity of a protein having an amino acid sequence that is different from the amino acid sequence as shown in SEQ ID NO: 2 can be evaluated in the following manner. Specifically, a gene encoding a protein to be evaluated is first introduced into a host cell in an expressible manner, and a protein is purified via chromatography or other means. Isocitrate and NADP are added as substrates to a buffer containing the protein to be evaluated. Thereafter, incubation is carried out at a desired temperature (e.g., 10 degrees C. to 60 degrees C.). After the completion of the reaction, the amount of substrates reduced and/or that of products (2-oxoglutarate) generated may be measured to evaluate the presence or absence and the degree of the NADP-dependent isocitrate dehydrogenase activity of the protein to be evaluated.

<Yeast>

In the present invention, target yeast strains in which expression of the NADP-dependent isocitrate dehydrogenase genes is to be reinforced are not particularly limited, provided that such strains have isobutanol biosynthesis pathways. Examples include yeast strains of the genus *Saccharomyces* (e.g., *Saccharomyces cerevisiae*), yeast strains of the genus *Candida*, yeast strains of the genus *Torulopsis*, yeast strains of the genus *Zygosaccharomyces*, yeast strains of the genus *Schizosaccharomyces*, yeast strains of the genus *Pichia*, yeast strains of the genus *Yarrowia*, yeast strains of the genus *Hansenula*, yeast strains of the genus *Kluyveromyces*, yeast strains of the genus *Debaryomyces*, yeast strains of the genus *Geotrichum*, yeast strains of the genus *Wickerhamia*, and yeast strains of the genus *Fellomyces*. Yeast strains may be wild-type yeast strains mentioned above, or mutant strains into which various types of mutations have been introduced. For example, mutant yeast strains in which expression levels of foreign genes are enhanced via gene recombination or mutagenesis can be used as host strains.

Also, mutant yeast strains that have been modified so as to allow the reaction, which naturally occurs in the mitochondria in the isobutanol biosynthesis pathway, to proceed in the cytoplasm may be used, as described above. Such mutant yeast strains are disclosed in WO 2011/019894. Mutant yeast strains disclosed therein can be used.

Further, target yeast strains in which expression of the NADP-dependent isocitrate dehydrogenase genes is to be reinforced are preferably mutant yeast strains lacking the functions of the NAD-dependent isocitrate dehydrogenase gene. In the case of *Saccharomyces cerevisiae*, for example, the IDH1 gene and the IDH2 gene that function in the mitochondria are known as NAD-dependent isocitrate dehydrogenase genes. By deleting either or both the IDH1 gene and the IDH2 gene, the enzyme activity of NAD-dependent isocitrate dehydrogenase that contributes to the reaction for generating 2-oxoglutarate from isocitrate in the mitochondria can be reduced, and the enzyme activity of NADP-dependent isocitrate dehydrogenase can be enhanced in contrast. Thus, the amount of NADPH supplied by the expression-reinforced NADP-dependent isocitrate dehydrogenase can be increased.

When the NADP-dependent isocitrate dehydrogenase gene is introduced into such yeast host cell in an expressible manner, such gene can be introduced into a yeast cell in the form of a common expression vector. Typically, a vector has a selectable marker gene, a cloning site, and control regions (a promoter and a terminator). Such vector is well-known in the art and commercially available.

A promoter contained in a vector may be a constitutive or inducible promoter, provided that it is functional in a yeast cell. The situation in which a promoter is functional is a situation in which a downstream gene can be transcribed in a yeast host cell. A promoter is not particularly limited. Examples thereof that can be used include the glyceraldehyde-3-phosphate dehydrogenase gene (TDH3) promoter, the 3-phosphoglycerate kinase gene (PGK1) promoter, and the hyperosmolarity response 7 gene (HOR7) promoter. The pyruvate decarboxylase gene (PDC1) promoter is particularly preferable because of its capacity for expressing the target downstream genes at high levels.

An expression vector can be introduced via various conventional techniques, such as electroporation (Meth. Enzym., 194, p. 182, 1990), the spheroplast method (Proc. Natl. Acad. Sci. U.S.A., 75, p. 1929, 1978), and the lithium acetate method (e.g., J. Bacteriology, 153, p. 163, 1983; Proc. Natl. Acad. Sci., U.S.A., 75, p. 1929, 1978; or Methods in Yeast Genetics, 2000 Edition: A Cold Spring Harbor Laboratory Course Manual), although techniques are not limited thereto.

<Production of Isobutanol>

The target yeast strains in which expression of the NADP-dependent isocitrate dehydrogenase genes is to be reinforced may be cultured in a medium containing a carbon source such as glucose, so that isobutanol biosynthesis is allowed to proceed. In this case, NADP-dependent isocitrate dehydrogenase is capable of supplying NADPH, which is used for the reaction for converting 2-acetolactate into 2,3-dihydroxy-isovalerate. This can prevent the isobutanol productivity resulting from depletion or reduction of NADPH in the isobutanol biosynthesis pathway from decreasing, and it can maintain isobutanol productivity at high levels.

Since synthesized isobutanol is present in a medium, cells may be separated from a medium via centrifugation or other means, and isobutanol can then be recovered from the supernatant fraction. Butanol can be recovered from the supernatant fraction by, for example, adding organic solvents such as ethyl acetate and methanol to the supernatant fraction and thoroughly stirring the mixture. An aqueous phase is separated from a solvent phase, and isobutanol can be extracted from a solvent phase.

EXAMPLE 1

Hereafter, the present invention is described in greater detail with reference to the examples, although the technical scope of the present invention is not limited to these examples.

<Construction of DNA Fragment Overexpressing the IDP2 Gene Localized in Mitochondria>

A DNA fragment comprising a terminator region of the HIS3 gene and a promoter region of the TDH3 gene was amplified via PCR using pCR-5U_PDC6-T_HIS3-P_TDH3-Ble-T_URA3-PDC1part-5U_PDC6 (the method for preparing the same is described in the reference example below) as a template. PCR was carried out using the TB3345 primer (5'-TGCGGCCGGCCGCAGCTTTGCAGAG-3': SEQ ID NO: 3) and the TB 1928 primer (5'-TTTGTTTGTTTATGT-GTGTTTATTCGAAAC-3': SEQ ID NO: 4).

With the use of the genome of the OC2 yeast strain (NBRC2260) as a template, a DNA fragment comprising a promoter region of the TDH2 gene, a DNA fragment comprising a mitochondrial transport signal of the COX4 gene, a DNA fragment comprising ORF and a terminator region of the IDP2 gene, and a DNA fragment comprising part of the PDC1 gene were amplified via PCR. Primers used for the above PCR procedure were designed with reference to the DNA sequence data of the *Saccharomyces* Genome Database (http://www.yeastgenome.org/), in such a manner that the amplified DNA fragments would contain an overlapping region of about 15 bp. PCR to amplify the DNA fragment comprising a promoter region of the TDH2 gene was carried out using the TB2704 primer (5'-CTTGACGGGTATTCT-GAGCATCTTAC-3': SEQ ID NO: 5) and the TB2595 primer (5'-TTTGTTTTGTTTGTTTGTGTGATGAATT-TAATTTG-3: SEQ ID NO: 6). PCR to amplify the DNA fragment comprising a mitochondrial transport signal of the COX4 gene was carried out using the TB2448 primer (5'-AACAAACAAAACAAAATGCTTTCACTACGTCAATC-3': SEQ ID NO: 7) and the TB2449 primer (5'-CT-TAATCTTTGTCATAAGAGCATATCTAGAGCTACACA-AAG-3': SEQ ID NO: 8). PCR to amplify the DNA fragment comprising ORF and a terminator region of the IDP2 gene was carried out using the TB2452 primer (5'-ATGACAAA-GATTAAGGTAGCTAACCCC-3': SEQ ID NO: 9) and the TB2092 primer (5'-GACCAAGTTAGCTGGTATATCG-GTCCTCTGTGTAG-3': SEQ ID NO: 10). PCR to amplify the DNA fragment comprising part of the PDC1 gene was carried out using the TB2814 primer (5'-CCAGCTAACTTG-GTCGACTTG-3': SEQ ID NO: 11) and the TB0115 primer (5'-TTGCAAAGAACCGTCACCAATG-3': SEQ ID NO: 12).

The mitochondrial transport signal sequence of the COX4 gene was predicted to be a region comprising 25 amino acid residues at the 5' end of the ORF in accordance with the method of O. Emanuelsson et al. (a prediction program based on the algorithm described in J. Mol. Biol. 300, 1005-1016, TargetP, http://www.cbs.dtu.dk/services/TargetP/).

With the use of pAUR101 (Takara Bio Inc.) as a template, a DNA fragment comprising ORF and a terminator region of the AUR1-C (aureobasidin resistant) gene was amplified via PCR. PCR was carried out using the TB 1972 primer (5'-ACATAAACAAACAAAATGGCAAAC-CCTTTTTCGAGATG-3': SEQ ID NO: 13) and the TB1973 primer (5'-AGAATACCCGTCAAGCTGGATAGAGCCT-CATCGTTAC-3': SEQ ID NO: 14).

Subsequently, the DNA fragment comprising the AUR1-C gene and the DNA fragment comprising a promoter region of the TDH2 gene amplified via PCR were bound to each other using the In-Fusion™ Advantage PCR Cloning Kit (Clontech), and the resultant was amplified via PCR using the TB 1972 primer and the TB2595 primer. The DNA fragment comprising a mitochondrial transport signal of the COX4 gene, the DNA fragment comprising ORF and a terminator region of the IDP2 gene, and the DNA fragment comprising part of the PDC1 gene were bound to each other using the TB2448 primer and the TB0115 primer, and the resultant was amplified via PCR. The two resulting DNA fragments were cloned into plasmids using the Zero Blunt TOPO PCR Cloning Kit (Invitrogen). Two DNA fragments amplified via PCR using the cloned plasmids as templates, a DNA fragment comprising a terminator region of the HIS3 gene, and the DNA fragment comprising a promoter region of the TDH3 gene were bound to each other using the In-Fusion™ Advantage PCR Cloning Kit, and the resulting DNA fragment was amplified via PCR using the TB 1932 primer and the TB0115 primer. The resulting DNA fragment amplified via PCR was cloned into a plasmid using the Zero Blunt TOPO PCR Cloning Kit. The resulting plasmid was designated as pCR -T_HIS3-P_TDH3-AUR1-C-P_TDH2-IDP2m-T_IDP2-PDC1part.

<Construction of DNA Fragment Overexpressing IDP2>

With the use of pCR-T_HIS3-P_TDH3-AUR1-C-P_TDH2-IDP2m-T_IDP2-PDC1part obtained above as a template, a plasmid lacking a mitochondrial transport signal of the COX4 gene fused to the IDP2 gene was constructed using PrimeSTAR MAX DNA Polymerase (Takara Bio Inc.). The resulting plasmid was designated as pCR-T_HIS3-P_TDH3-AUR1-C-P_TDH2-IDP2-T_IDP2-PDC1part. In this case, the TB2091 primer (5'-AACAAACAAAA-CAAAATGACAAAGATTAAGGTAGCTAACCC-3': SEQ ID NO: 15) and the TB2595 primer were used.

<Preparation of Strains Overexpressing the IDP2 Gene Localized in Mitochondria>

At the outset, a DNA fragment other than a pCR-Blunt II TOPO vector region was amplified via PCR using pCR-5U_PDC6-T_HIS3-P_TDH3-Ble-T_URA3-PDC1part-5U_PDC6 (the method for preparing the same is described in the reference examples below) as a template. PCR was carried out using the TB0948 primer and the TB0735 primer (see reference examples for the primer sequences). The *Saccharomyces cerevisiae* OC2-T strain was transformed with the amplified DNA fragment (J. Ferment. Bioeng. 81:98-103) using the Frozen-EZ Yeast Transformation II kit (Zymo Research) in accordance with the protocols included in the kit. After transformation, the resultants were sowed on a YPD plate containing zeocin (300 micrograms/ml), culture was conducted at 30 degrees C. for 5 days to obtain transformants, and the resulting strains were designated as the Uz180 strains.

Separately, a DNA fragment other than a pCR-Blunt II TOPO vector region was amplified via PCR using pCR-T_HIS3-P_TDH3-AUR1-C-P_TDH2-IDP2m-T_IDP2-PDC1part obtained above as a template. PCR was carried out using the TB 1932 primer and the TB0115 primer. The Uz180 strain obtained above was transformed with the amplified DNA fragment using the Frozen-EZ Yeast Transformation II kit. After transformation, the resultants were sowed on a YPD plate containing aureobasidin (1.5 micrograms/ml), culture was conducted at 30 degrees C. for 5 days to obtain transformants, and the resultants were designated as the Uz251 strains.

<Construction of DNA Fragment Overexpressing the IDP2 Genes Localized in Mitochondria And Disrupting the IDH1 Gene>

A DNA fragment comprising a promoter region of the TDH3 gene, a terminator region of the HIS3 gene, the pCR-Blunt II TOPO vector sequence, and part of the PDC1 gene was amplified via PCR using pCR-T_HIS3-P_TDH3-AUR1-C-P_TDH2-IDP2m-T_IDP2-PDC1part obtained above as a template. PCR was carried out using the TB 1928 primer and the TB 1147 primer (5'-CCAGCTAACTTGGTCGACTTG-3': SEQ ID NO: 16).

A DNA fragment comprising ORF, a promoter region, and a terminator region of the AUR1-C gene was amplified via PCR using pAUR101 as a template. PCR was carried out using the TB2819 primer (5'-CGTGGCTGCGAGC- GAAGCCATCGCACTGTACCA-3': SEQ ID NO: 17) and the TB2859 primer (5'-CTGGATAGAGCCTCATCGTTA- CAC-3': SEQ ID NO: 18).

With the use of the genome DNA of the OC2 yeast strain as a template, a DNA fragment comprising a mitochondrial transport signal of the COX4 gene and a terminator region of the IDP2 gene, a DNA fragment comprising a terminator region of the ERO1 gene, and a DNA fragment comprising a promoter region of the HOR7 gene were amplified via PCR. PCR primers were designed in such a manner that the amplified DNA fragments would contain an overlapping region of about 15 bp. PCR to amplify the DNA fragment comprising a mitochondrial transport signal of the COX4 gene, the IDP2 gene, and a terminator region thereof was carried out using the TB2863 primer (5'-ACATAAACAAACAAAAT- GCTTTCACTACGTCAATCTATAAG-3': SEQ ID NO: 19) and the TB2862 primer (5'-AATCACTCCTCATTG- TATATCGGTCCTCTGTGTAG-3': SEQ ID NO: 20). PCR to amplify the DNA fragment comprising a terminator region of the ERO1 gene was carried out using the TB2429 primer (5'-CAATGAGGAGTGATTTTACACAAAAAG-3': SEQ ID NO: 21) and the TB2433 primer (5'-TAATAAAAGAG- CAACACAGTTTATCTTATATG-3': SEQ ID NO: 22). PCR to amplify the DNA fragment comprising a promoter region of the HOR7 gene was carried out using the TB4032 primer (5'-ACATAAACAAACAAATTTTATTATT- AGTCTTTTTTTTTTTTGACAATATC-3': SEQ ID NO: 23) and the TB2654 primer (5'-TCGCTCGCAGCCACGGGT-3': SEQ ID NO: 24).

Subsequently, the DNA fragment comprising a promoter region of the TDH3 gene, a terminator region of the HIS3 gene, the pCR-Blunt II TOPO vector sequence, and part of the PDC1 gene, the DNA fragment comprising a promoter region of the HOR7 gene, and the DNA fragment comprising ORF, a promoter region, and a terminator region of the AUR1-C gene were subjected to cloning using the In-Fusion™ Advantage PCR Cloning Kit (Takara Bio Inc.). The resulting plasmid was designated as pCR-T_HIS3-P_TDH3-HOR7_P- AUR1-PDC1part. Subsequently, a linear DNA fragment cleaved between a promoter region of the TDH3 gene and a promoter region of the HOR7 gene was amplified via PCR using pCR-T_HIS3-P_TDH3-HOR7_P-AUR1-PDC1part as a template. The TB1928 primer and the TB2432 primer (5'- GTTGCTCTTTTATTATTAGTCTTTTTTTTTTTTG-3': SEQ ID NO: 25) were used. The resulting DNA fragment, a DNA fragment comprising a mitochondrial transport signal of the COX4 gene, the IDP2 gene, and a terminator region thereof, and a DNA fragment comprising a terminator region of the ERO1 gene were subjected to cloning using the In-Fusion™ Advantage PCR Cloning Kit. The resulting plasmid was designated as pCR-T_HIS3-P_TDH3-IDP2m-T_IDP2- ERO1_T-HOR7_P-AUR1-PDC1part.

A DNA fragment comprising the IDH1 gene and the 5' upstream and 3' downstream untranslated regions thereof was amplified via PCR, and the resultant was subjected to cloning using the Zero Blunt TOPO PCR Cloning Kit. PCR was carried out using the TB2789 primer (5'-CGGTAGCGCT- CATTCTGATG-3': SEQ ID NO: 26) and the TB2791 primer (5'-TCAAGCAAAATGGGAGGGTAG-3': SEQ ID NO: 27). A DNA fragment comprising the 5' upstream and 3' downstream untranslated regions and a region including pCR- Blunt II TOPO of the IDH1 gene was amplified using the above plasmid as a template. The TB2792 primer (5'-TAA- CATTCAACGCTATTTTCTCTTACAATTATGGAGG-3': SEQ ID NO: 28) and the TB2860 primer (5'-TGAGGCTC- TATCCAGTGAAAACAATTCCCCTTTTTTTTGTTC-3': SEQ ID NO: 29) were used. Subsequently, the DNA fragment comprising a promoter region of the TDH3 gene, a mitochondrial transport signal of the COX4 gene, the IDP2 gene, and a terminator region thereof, a terminator region of the ERO1 gene, and a promoter region of the HOR7 gene and the DNA fragment comprising ORF, a promoter region, and a terminator region of the AUR1-C gene were amplified via PCR using pCR-T_HIS3-P_TDH3-IDP2m-T_IDP2-ERO1_T- HOR7_P-AUR1-PDC1part obtained above as a template. PCR was carried out using the TB2717 primer and the TB2859 primer. The resulting DNA fragment and a DNA fragment comprising the 5' upstream and 3' downstream untranslated regions and a region including pCR-Blunt II TOPO of the IDH1 gene were subjected to cloning using the In-Fusion™ Advantage PCR Cloning Kit. The resulting plasmid was designated as pCR-5U_IDH1-P_TDH3-IDP2m- T_IDP2-ERO1_T-HOR7_P-AUR1-3U_IDH3.

<Preparation of Strains Overexpressing the IDP2 Gene Localized in Mitochondria and Carrying Heterozygous Disruption of The IDH1 Gene>

A DNA fragment other than a pCR-Blunt II TOPO vector region was amplified via PCR using pCR-5U_IDH1- P_TDH3-IDP2m-T_IDP2-ERO1_T-HOR7_P-AUR1- 3U_IDH3 obtained above as a template. PCR was carried out using the TB2789 primer and the TB2791 primer. The OC2-T strain was transformed with the amplified DNA fragment using the Frozen-EZ Yeast Transformation II kit. After transformation, the resultants were sowed on a YPD plate containing aureobasidin (1.5 micrograms/ml), culture was conducted at 30 degrees C. for 5 days to obtain transformants, and the resulting strains were designated as the Uz487 strains. Since the OC2-T strains are diploids, the Uz487 strains carry heterozygous disruption of the IDH1 gene.

<Construction of DNA Fragment Overexpressing the ILV3, ILV6, and ADH2 Genes Localized in Cytoplasm and Disrupting the PDC5 Gene>

At the outset, a DNA fragment comprising the PDC5 gene and the 5' upstream and 3' downstream untranslated regions thereof were amplified via PCR using the genomic DNA of the OC2 yeast strain as a template, and a DNA fragment cleaved at the pUC19 multicloning site and comprising full-length pUC19 was amplified via PCR using the pUC19 plasmid as a template. PCR primers were designed in such a manner that the amplified fragments would contain an overlapping region of about 15 bp.

PCR to amplify the DNA fragment comprising the 5' upstream and 3' downstream untranslated regions of the PDC5 gene was carried out using the TB1511 primer (5'- AAGCCTCCACTGCCATCACT-3': SEQ ID NO: 30) and the TB1566 primer (5'-AAAACCACTAAGTGACAAA- GAACTACGC-3': SEQ ID NO: 31). PCR to amplify the DNA fragment cleaved at the pUC19 multicloning site and comprising full-length pUC19 was carried out using the TB2204 primer (5'-TCACTTAGTGGTTTTGATCCTCTA- GAGTCGAC-3': SEQ ID NO: 32) and the TB2205 primer (5'-TGGCAGTGGAGGCTTGATCCCCGGGTACCGAGC- 3': SEQ ID NO: 33). The DNA fragment amplified via PCR was subjected to cloning using the In-Fusion™ Advantage PCR Cloning Kit (Takara Bio Inc.), and the resulting plasmid was designated as pUC19-5U_PDC5-PDC5-3U_PDC5.

Subsequently, a DNA fragment comprising the 5' upstream and 3' downstream untranslated regions of the PDC5 gene and a region comprising pUC19 was amplified via PCR using pUC19-5U_PDC5-PDC5-3U_PDC5 as a template, and a DNA fragment comprising a CYC1 terminator region, a DNA fragment comprising a TEF1 promoter region, and a DNA fragment comprising the ADH2 gene were amplified via PCR using genomic DNA of the BY4742 yeast strain (Open Biosystems) as a template. PCR primers were designed in such a manner that the amplified fragments would contain an overlapping region of about 15 bp.

PCR to amplify the DNA fragment comprising the 5' upstream and 3' downstream untranslated regions and a region comprising pUC19 of the PDC5 gene was carried out using the TB2238 primer (5'-GGGGCCTGTCTTAA-GAGAAAGAGAGGAAAGGACTTACTAC-3': SEQ ID NO: 34) and the TB3048 primer (5'-GGTTAAAGATTAGCT-TCTAATATTTTAGGTGG-3': SEQ ID NO: 35). PCR to amplify the DNA fragment comprising the CYC1 terminator region was carried out using the TB2236 primer and the TB3189 primer (5'-GCTATGGTGTGTGGGCTGCAG-GAATTCGATATCAAGC-3': SEQ ID NO: 36). PCR to amplify the DNA fragment comprising the TEF1 promoter region was carried out using the TB2210 primer (5'-CCCA-CACACCATAGCTTCAAAATG-3': SEQ ID NO: 37) and the TB2123 primer (5'-TAGATTGCTATGCTTTCTT-TCTAATGAGC-3': SEQ ID NO: 38). PCR to amplify the DNA fragment comprising the ADH2 gene was carried out using the TB 1960 primer (5'-AAGCATAG-CAATCTAATCTAAAGAATGTCTATTCCAGAAACTCA-3': SEQ ID NO: 39) and the TB4023 primer (5'-AGC-TAATCTTTAACCCTTATTTAGAAGTGTCAACAACGT-ATC-3': SEQ ID NO: 40). The four DNA fragments amplified via PCR were subjected to cloning using the In-Fusion™ Advantage PCR Cloning Kit, and the resulting plasmid was designated as pUC19-5U_PDC5-T_CYC1-P_TEF1-ADH2-3U_PDC5.

Subsequently, a linear DNA fragment cleaved between the 3' downstream untranslated region of the ADH2 gene and the PDC5 gene was amplified via PCR using pUC19-5U_PDC5-T_CYC1-P_TEF1-ADH2-3U_PDC5 as a template, a DNA fragment comprising the HIS3 terminator region and a DNA fragment comprising the CYC1 promoter region were amplified via PCR using genomic DNA of the BY4742 yeast strain as a template, and a DNA fragment comprising the G418 gene was amplified via PCR using pBG418-LDHKCB described in Appl. Environ. Microbiol., 71 (5): 2789-2792 as a template. PCR primers were designed in such a manner that the amplified fragments would contain an overlapping region of about 15 bp.

PCR to amplify the linear DNA fragment cleaved between the 3' downstream untranslated region of the ADH2 gene and the PDC5 gene was carried out using the TB2126 primer (5'-CTGCGGCCGGCCGCACTTATTTAGAAGT-GTCAACAACGTATC-3': SEQ ID NO: 41) and the TB3048 primer. PCR to amplify the DNA fragment comprising the HIS3 terminator region was carried out using the TB3345 primer (5'-TGCGGCCGGCCGCAGCTTTGCAGAG-3': SEQ ID NO: 42) and the TB2490 primer (5'-AGAGCGCGC-CTCGTTCAG-3': SEQ ID NO: 43). PCR to amplify the DNA fragment comprising the CYC1 promoter region was carried out using the TB 1207 primer (5'-AACGAGGCGCGCTC-TACGACATCGTCGAATATGAT-3': SEQ ID NO: 44) and the TB2465 primer (5'-TATTAATTTAGTGTGTG-TATTTGTGTTTGTGTG-3': SEQ ID NO: 45). PCR to amplify the DNA fragment comprising the G418 gene was carried out using the TB2776 primer (5'-CACACTAAAT-TAATAATGAGCCATATTCAACGGG-3': SEQ ID NO: 46) and the TB4024 primer (5'-AGCTAATCTTTAACCTTA-CAACCAATTAACCAATTCTG-3': SEQ ID NO: 47). The four DNA fragments amplified via PCR were subjected to cloning using the In-Fusion™ Advantage PCR Cloning Kit, and the resulting plasmid was designated as pUC19-5U_PDC5-T_CYC1-P_TEF1-ADH2-T_HIS3-P_CYC1-G418-3U_PDC5.

Subsequently, a linear DNA fragment cleaved between the 3' downstream untranslated region of the G418 gene and the PDC5 gene and a DNA fragment comprising the URA3 terminator region were amplified via PCR using pUC19-5U_PDC5-T_CYC1-P_TEF1-ADH2-T_HIS3-P_CYC1-G418-3U_PDC5 as a template, and a DNA fragment comprising the TDH2 promoter region and a DNA fragment comprising the ILV3 gene localized in the cytoplasm and a terminator region were amplified via PCR using genomic DNA of the OC2 yeast strain as a template. The ILV3 gene localized in the cytoplasm comprises a nucleotide sequence resulting from substitution of a region encoding a putative mitochondrial transport signal comprising 19 amino acid residues from the 5' end with a codon encoding methionine. The mitochondrial transport signal was predicted using the TargetP prediction program. PCR primers were designed in such a manner that the amplified fragments would contain an overlapping region of about 15 bp.

PCR to amplify the linear DNA fragment cleaved between the 3' downstream untranslated region of the G418 gene and the PDC5 gene was carried out using the TB2122 primer (5'-TTTAGTAGACATGCATTACAACCAAT-TAACCAATTCTG-3': SEQ ID NO: 48) and the TB3048 primer. PCR to amplify the DNA fragment comprising the URA3 terminator region was carried out using the TB2121 primer (5'-TGCATGTCTACTAAACTCACAAATTAGAG-CTTCAATT-3': SEQ ID NO: 49) and the TB2026 primer (5'-GCTCAGAATACCCGTCAAGGGGTAATAACTGAT-ATAATTAAATTGAAG-3': SEQ ID NO: 50). PCR to amplify the DNA fragment comprising the TDH2 promoter region was carried out using the TB2704 primer and the TB2595 primer. PCR to amplify the DNA fragment comprising the ILV3 gene localized in the cytoplasm and a terminator region was carried out using the TB2014 primer (5'-AA-CAAACAAAACAAAATGGCAAAGAAGCT-CAACAAGTAC-3': SEQ ID NO: 51) and the TB4025 primer (5'-AGCTAATCTTTAACCATTTCGTAGAT-TATAATTAAGGCGAC-3': SEQ ID NO: 52). The four DNA fragments amplified via PCR were subjected to cloning using the In-Fusion™ Advantage PCR Cloning Kit, and the resulting plasmid was designated as pUC19-5U_PDC5-T_CYC1-P_TEF1-ADH2-T_HIS3-P_CYC1-G418-T_URA3-P_TD H2-ILV3c-T_ILV3-3U_PDC5.

Subsequently, a linear DNA fragment cleaved between the DNA fragment comprising the ILV3 terminator region and the DNA fragment comprising the 3' downstream untranslated region of the PDC5 gene were amplified via PCR using pUC19-5U_PDC5-T_CYC1-P_TEF1-ADH2-T_HIS3-P_CYC1-G418-T_URA3-P_TD H2-ILV3c-T_ILV3-3U_PDC5 as a template, and a DNA fragment comprising the ILV6 gene localized in the cytoplasm and a terminator region and a DNA fragment comprising the PDC1 promoter region were amplified via PCR using the genomic DNA of the OC2 yeast strain as a template. The DNA fragment comprising the ILV6 gene was amplified via PCR using the genomic DNA of the OC2 yeast strain as a template. The ILV6 gene localized in the cytoplasm comprises a nucleotide sequence resulting from substitution of a region encoding a putative mitochondrial transport signal comprising 40 amino acid residues from the 5' end with a codon encoding methionine. The mitochondrial transport signal was predicted using the TargetP prediction program. PCR primers were designed in such a manner that the amplified fragments would contain an overlapping region of about 15 bp.

PCR to amplify the linear DNA fragment cleaved between the DNA fragment comprising the ILV3 terminator region and the DNA fragment comprising the 3' downstream untranslated region of the PDC5 gene was carried out using the TB3052 primer (5'-ATTTCGTAGATTATAATTAAGGC-GACTTTTC-3': SEQ ID NO: 53) and the TB2237 primer (5'-CACGGTGGAAGAAGGGGTTAAAGATT-AGCTTCTAATATTTTAGG-3': SEQ ID NO: 54). PCR to amplify the DNA fragment comprising the ILV6 gene localized in the cytoplasm and a terminator region was carried out using the TB4022 primer (5'-TATAATCTACGAAAT-TAATAAGAAAGGTGACCGTG-3': SEQ ID NO: 55) and the TB2015 primer (5'-GTCAAATCAATCAAAATG-GCAACAAGACCTCCCTTG-3': SEQ ID NO: 56). PCR to amplify the DNA fragment comprising the PDC1 promoter region was carried out using the TB2010 primer (5'-TTTGATTGATTTGACTGTGTTATTTTGC-3': SEQ ID NO: 57) and the TB2057 primer (5'-CCTTCTTCCACCGT-GTCAAGC-3': SEQ ID NO: 58). The four DNA fragments amplified via PCR were subjected to cloning using the In-Fusion™ Advantage PCR Cloning Kit, and the resulting plasmid was designated as pUC19-5U_PDC5-T_CYC1-P_TEF1-ADH2-T_HIS3-P_CYC1-G418-T_URA3-P_TDH2-ILV3c-T_ILV3-ILV6_T-ILV6c-PDC1_P-3U_PDC5.

<Preparation of DNA Fragment Overexpressing the ILV5, ILV2, and ARO10 Genes Localized in Cytoplasm and Disrupting the PDC5 Gene>

Subsequently, a DNA fragment comprising the 5' upstream and 3' downstream untranslated regions and a region comprising pUC19 of the PDC5 gene was amplified via PCR using pUC19-5U_PDC5-PDC5-3U_PDC5 as a template, and a DNA fragment comprising the TDH3 terminator region, a DNA fragment comprising the ILV5 gene localized in the cytoplasm and a terminator region, and a DNA fragment comprising the ILV2 gene localized in the cytoplasm and a terminator region were amplified via PCR using the genomic DNA of the OC2 yeast strain as a template. The ILV5 gene localized in the cytoplasm comprises a nucleotide sequence resulting from substitution of a region encoding a putative mitochondrial transport signal comprising 34 amino acid residues from the 5' end with a codon encoding methionine. The ILV2 gene localized in the cytoplasm comprises a nucleotide sequence resulting from substitution of a region encoding a putative mitochondrial transport signal comprising 54 amino acid residues from the 5' end with a codon encoding methionine. The mitochondrial transport signal was predicted using the TargetP prediction program. PCR primers were designed in such a manner that the amplified fragments would contain an overlapping region of about 15 bp.

PCR to amplify the DNA fragment comprising the 5' upstream and 3' downstream untranslated regions and a region comprising pUC19 of the PDC5 gene was carried out using the TB2739 primer (5'-AGAAAGAGAGGAAAG-GACTTACTACAGTATATTG-3': SEQ ID NO: 59) and the TB3048 primer. PCR to amplify the DNA fragment comprising the TDH3 terminator region was carried out using the TB2738 primer (5'-CTTTCCTCTCTTTCTCTATTTTC-GAGGACCTTGTCACC-3': SEQ ID NO: 60) and the TB3061 primer (5'-ACGGGCAGCTG-GCATTTTGTTTGTTTATGTGTGTTTATTCGAAAC-3': SEQ ID NO: 61). PCR to amplify the DNA fragment comprising the ILV5 gene localized in the cytoplasm and a terminator region was carried out using the TB3060 primer (5'-ATGCCAGCTGCCCGTTTC-3': SEQ ID NO: 62) and the TB4026 primer (5'-AACCGCTTTATAGAATATGTA-CACGTATATGTGACGAG-3': SEQ ID NO: 63). PCR to amplify the DNA fragment comprising the ILV2 gene localized in the cytoplasm and a terminator region was carried out using the TB4027 primer (5'-TTCTATAAAGCGGTTAAAT-TCGTATTGGC-3': SEQ ID NO: 64) and the TB4028 primer (5'-AGCTAATCTTTAACCATGCCAGAGCCTGCTCCA-3': SEQ ID NO: 65). The four DNA fragments amplified via PCR were subjected to cloning using the In-Fusion™ Advantage PCR Cloning Kit, and the resulting plasmid was designated as pUC19-5U_PDC5-P_TDH3-ILV5c-ILV2c-3U_PDC5.

Subsequently, a linear DNA fragment cleaved between the ILV2 gene and a DNA fragment comprising the 3' downstream untranslated region of the PDC5 gene was amplified via PCR using pUC19-5U_PDC5-P_TDH3-ILV5c-ILV2c-3U_PDC5 as a template, and a DNA fragment comprising the FBA1 promoter region, a DNA fragment comprising the ADH1 promoter region, and a DNA fragment comprising the ARO10 gene were amplified via PCR using the genomic DNA of the OC2 yeast strain as a template. PCR primers were designed in such a manner that the amplified fragments would contain an overlapping region of about 15 bp.

PCR to amplify a linear DNA fragment cleaved between the ILV2 gene and a DNA fragment comprising the 3' downstream untranslated region of the PDC5 gene was carried out using the TB2277 primer (5'-TAATACATATTCAAAATGC-CAGAGCCTGCTCCA-3': SEQ ID NO: 66) and the TB3048 primer. PCR to amplify the DNA fragment comprising the FBA1 promoter region was carried out using the TB2276 primer (5'-TTTGAATATGTATTACTTGGTTATGGT-TATATATGAC-3': SEQ ID NO: 67) and the TB3085 primer (5'-ACTGGTAGAGAGCGACTTTGTATGC-3': SEQ ID NO: 68). PCR to amplify the DNA fragment comprising the ADH1 promoter region was carried out using the TB2243 primer (5'-CAAAGTCGCTCTCTAC-CAGTCGCTTTCAATTCATTTGGGTG-3': SEQ ID NO: 69) and the TB2298 primer (5'-GGTGCCATTGTATAT-GAGATAGTTGA-3': SEQ ID NO: 70). PCR to amplify the DNA fragment comprising the ARO10 gene was carried out using the TB2297 primer (5'-ATATACAATGGCACCTGT-TACAATT-3': SEQ ID NO: 71) and the B4029 primer (5'-AGCTAATCTTTAACCCTATTTTT-TATTTCTTTTAAGTGCCG-3': SEQ ID NO: 72). The four DNA fragments amplified via PCR were subjected to cloning using the In-Fusion™ Advantage PCR Cloning Kit, and the resulting plasmid was designated as pUC 19-5U_PDC5-P_TDH3-ILV5c-T_ILV5-ILV2_T-ILV2c-P_FBA1-P_ADH1-ARO 10-3U_PDC5.

Subsequently, a linear DNA fragment cleaved between the ARO10 gene and a DNA fragment comprising the 3' downstream untranslated region of the PDC5 gene was amplified via PCR using pUC 19-5U_PDC5-P_TDH3-ILV5cy-T_ILV5-ILV2_T-ILV2cy-P_FBA1-P_ADH 1-A RO10-3U_PDC5 as a template, and a DNA fragment comprising the CYC1 terminator region and a DNA fragment comprising the TEF1 promoter region were amplified via PCR using the genomic DNA of the OC2 yeast strain as a template. PCR primers were designed in such a manner that the amplified fragments would contain an overlapping region of about 15 bp.

PCR to amplify the linear DNA fragment cleaved between the ARO10 gene and a DNA fragment comprising the 3' downstream untranslated region of the PDC5 gene was carried out using the TB4030 primer (5'-GGGGCCTGTCT-TAAGCTATTTTTTATTTCTTTTAAGTGC-3': SEQ ID NO: 73) and the TB2245 primer (5'-AATCTAATCTAAA-GAGGGTTAAAGATTAGCTTCTAATATTTTAGGTG-3': SEQ ID NO: 74). PCR to amplify the DNA fragment comprising the CYC1 terminator region was carried out using the TB2236 primer (5'-CTTAAGACAGGCCCCTTTTC-CTTTG-3': SEQ ID NO: 75) and the TB3189 primer. PCR to amplify the DNA fragment comprising the TEF1 promoter region was carried out using the TB2210 primer and the TB2269 primer (5'-TCTTTAGATTAGATTGCTAT-GCTTTCTTTCTAATGAGCAAG-3': SEQ ID NO: 76). The three DNA fragments amplified via PCR were subjected to cloning using the In-Fusion™ Advantage PCR Cloning Kit, and the resulting plasmid was designated as pUC 19-5U_PDC5-P_TDH3-ILV5c-T_ILV5-ILV2_T-ILV2c-P_FBA1-P_ADH1-ARO 10-T_CYC1-P_TEF1-3U_PDC5.

<Preparation of Strains Overexpressing the ILV3, ILV6, ADH2, ILV5, ILV2, and ARO10 Genes Localized in Cytoplasm and Disrupting the PDC5 Gene>

A DNA fragment comprising a region from the CYC1 terminator region to the 3' downstream untranslated region of the PDC5 gene was amplified via PCR using pUC19-5U_PDC5-T_CYC1-P_TEF1-ADH2-T_HIS3-P_CYC1-G418-T_URA3-P_TD H2-ILV3c-T_ILV3-ILV6 T-ILV6c-PDC1_P-3U_PDC5 obtained above as a template, and a DNA fragment comprising a region from the 5' upstream untranslated region to the TEF1 promoter region of the PDC5 gene was amplified via PCR using pUC 19-5U_PDC5-P_TDH3-ILV5c-T_ILV5-ILV2_T-ILV2c-P_FBA1-P_ADH1-ARO 10-T_CYC1-P_TEF1-3U_PDC5 as a template. PCR was carried out using the TB2236 primer and the TB 1566 primer or the TB 1511 primer and the TB2269 primer, respectively. Since the amplified fragments have overlapping sequences in the CYC1 terminator region and in the TEF1 promoter region, homologous recombination takes place at three sites; i.e., the PDC5 locus in the 5' upstream untranslated region, the CYC1 terminator region or TEF1 promoter region, and the PDC5 gene locus in the 3' downstream untranslated region, when the above fragments are simultaneously transformed, and all genes are introduced into the genomes. The OC2-T strain was transformed with the amplified DNA fragment using the Frozen-EZ Yeast Transformation II kit. After transformation, the resultants were sowed on a YPD plate containing G418 (200 micrograms/ml), culture was conducted at 30 degrees C. for 5 days to obtain transformants, and the resulting strains were designated as the Uz258 strains.

<Preparation of Strains Overexpressing the ILV3, ILV6, ADH2, ILV5, ILV2, ARO10, and IDP2 Genes Localized in Cytoplasm and Disrupting the PDC5 Gene>

A DNA fragment other than a pCR-Blunt II TOPO vector region was amplified via PCR using pCR-5U_PDC6-T_HIS3-P_TDH3-Ble-T_URA3-PDC1part-5U_PDC6 obtained above as a template. PCR was carried out using the TB0948 primer and the TB0735 primer. The Uz258 strain was transformed with the amplified DNA fragment using the Frozen-EZ Yeast Transformation II kit. After transformation, the resultants were sowed on a YPD plate containing zeocin (300 micrograms/ml), culture was conducted at 30 degrees C. for 5 days to obtain transformants, and the resulting strains were designated as the Uz430 strains.

Also, a DNA fragment other than a pCR-Blunt II TOPO vector region was amplified via PCR using pCR-T_HIS3-P_TDH3-AUR1-C-P_TDH2-IDP2-T_URA3-PDC1part as a template. PCR was carried out using the TB 1932 primer and the TB0115 primer. The Uz430 strain was transformed with the amplified DNA fragment using the Frozen-EZ Yeast Transformation II kit. After transformation, the resultants were sowed on a YPD plate containing aureobasidin (1.5 micrograms/ml), culture was conducted at 30 degrees C. for 5 days to obtain transformants, and the resulting strains were designated as the Uz443 strains.

<Fermentation Test>

At the outset, the resulting transformants were seeded on YPD medium (10 g/l yeast extract, 20 g/l peptone, and 20 g/l glucose), and shake culture was conducted at 30 degrees C. for 24 hours. After the completion of culture, cells were recovered via centrifugation at 2,000 g for 3 minutes.

Subsequently, 10 ml or 30 ml of glucose medium (200 g/l glucose and 10 g/l yeast extract) was introduced into a 100-ml flask, cells were seeded therein to a cell density of 2.7 g/l of cells on a dry basis, fermentation was carried out at 80 rpm and 34 degrees C. (shake width: 35 mm), and sampling was carried out two times at 5:00 pm and at 12:00 midnight (the higher concentration is shown). Isobutanol in the fermentation liquid was assayed using a gas chromatography apparatus (GC-2010, Shimadzu Corporation) under the conditions described below.

Columns: J & W Capillary Columns, DB-1 (30 m×0.32 mm (i.d.); membrane thickness: 1 micrometer)

Gas chromatographic parameters were as follows: column temperature: 40 degrees C.; equilibration time: 2 minutes; vaporizing chamber temperature: 250 degrees C.; detector temperature: 300 degrees C.; sampling time: 1 minute; split mode: splitless; carrier pressure: 58.9 kPa; column flow: 1.79 ml/min; linear velocity: 30 cm/sec; total flow: 4.8 ml/min; oven temperature: maintained at 40 degrees C. for 2 minutes, raised to 70 degrees C. at a rate of 5 degrees C./min, and then raised to 250 degrees C. at a rate of 50 degrees C./min and kept at that temperature for 1 minute.

<Results and Discussion>

Figure 3:
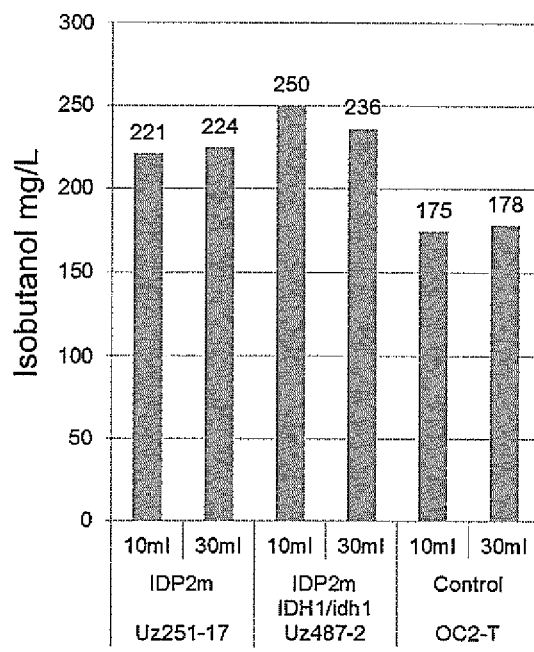
FIG. 3 is a characteristic diagram showing the results of quantification of isobutanol upon biosynthesis of a recombinant yeast strain into which an NADP-dependent isocitrate dehydrogenase gene is introduced in the mitochondria in an expressible manner.
Figure 4:
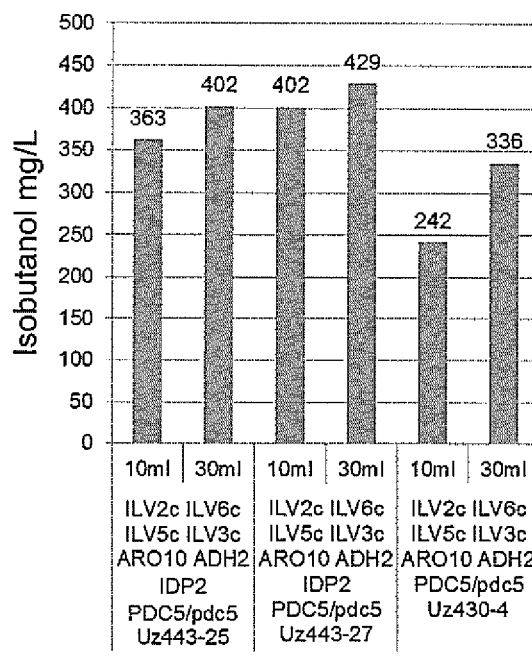
FIG. 4 is a characteristic diagram showing the results of quantification of isobutanol upon biosynthesis of a recombinant yeast strain comprising the NADP-dependent isocitrate dehydrogenase gene introduced in the cytoplasm in an expressible manner and allowing a biosynthesis reaction from glucose to isobutanol to proceed in the cytoplasm.

The results of fermentation tests are shown in FIGS. 3 and 4.

As shown in FIG. 3, the Uz251-17 strain comprising the IDP2 gene encoding the NADP-dependent isocitrate dehydrogenase overexpressed in the mitochondria exhibited an improvement in isobutanol yield. In addition, the Uz487 strain comprising the IDP2 gene overexpressed in the mitochondria and carrying heterozygous disruption of the IDH1 gene encoding one of the NAD-dependent isocitrate dehydrogenase IDH subunits localized in the mitochondria exhibited a further improvement in isobutanol yield, compared with the Uz251-17 strain. This is considered to result from the increased amount of NADPH supplied as a result of lowered enzyme activity of the NAD-dependent isocitrate dehydrogenase together with improved enzyme activity of the NADP-dependent isocitrate dehydrogenase in the mitochondria.

A biosynthesis reaction for converting pyruvate into 2-keto-isovalerate in the isobutanol biosynthesis pathway is naturally allowed to proceed in the mitochondria. In the case of the Uz430 strain comprising the ILV2, ILV6, ILV5, and ILV3 genes, which are isobutanol-producing pathway genes naturally expressed in the mitochondria, expressed in the cytoplasm, a biosynthesis reaction for converting pyruvate into 2-keto-isovalerate is allowed to proceed in the cytoplasm. The Uz443 strain comprising isobutanol-producing pathway genes (i.e., the ILV2, ILV6, ILV5, and ILV3 genes) and the IPD2 gene expressed in the cytoplasm exhibited an improvement in isobutanol yield, compared with the Uz430 strain (FIG. 4). The results demonstrate that isobutanol yield can be improved by reinforcing expression of the NADP-dependent isocitrate dehydrogenase gene in tissue in which a biosynthesis reaction for converting pyruvate into 2-keto-isovalerate is allowed to proceed.

REFERENCE EXAMPLE

In the Reference Example, a process for preparing pCR-5U_PDC6-T_HIS3-P_TDH3-Ble-T_URA3-PDC1part-5U_PDC6 used in the examples is described. This plasmid serves as a scaffold into which DNA fragments overexpressing the IPD2 genes are introduced in the examples above. In order to introduce a DNA fragment amplified using pCR- T_HIS3-P_TDH3-AUR1-C-P_TDH2-IDP2m-T_IDP2-PDC1part prepared in the examples as a template and the TB 1932 primer and the TB0115 primer into the genome of the OC2 strain, specifically, sequences at both 5' and 3' ends of the DNA fragment, which are homologous recombination regions, are required to exist in the vicinity of the chromosomes. Accordingly, a DNA fragment used for introducing a DNA fragment comprising a terminator region of the HIS3 gene and the promoter region of the TDH3 gene and a DNA fragment comprising part of the PDC1 gene into a site upstream of the PDC6 gene was prepared.

With the use of the genome of the OC2 yeast strain as a template, a DNA fragment comprising the 5' upstream untranslated region of the PDC6 gene and part of the PDC6 gene was first amplified, the resultant was subjected to cloning using the Zero Blunt TOPO PCR Cloning Kit, and the product was designated as pCR-5U_PDC6. PCR was carried out using the TB0948 primer (5'-GTTGAAGTCGCCTGG-TAGCC-3': SEQ ID NO: 77) and the TB0735 primer (5'-CGGTGATCCCCTTGAAAAAG-3': SEQ ID NO: 78).

With the use of the genome of the OC2 yeast strain as a template, a DNA fragment comprising a terminator region of the HIS3 gene, a DNA fragment comprising a promoter region of the TDH3 gene, a DNA fragment comprising a terminator region of the URA3 gene, and a DNA fragment comprising part of the PDC1 gene were amplified via PCR.

PCR to amplify the DNA fragment comprising a terminator region of the HIS3 gene was carried out using the TB 1401 primer (5'-TGCGGCCGGCCGCAGC-3': SEQ ID NO: 79) and the TB 1433 primer (5'-CGCTAACATTCAACGCTAA-GAGCGCGCCTCGTTC-3': SEQ ID NO: 80). PCR to amplify the DNA fragment comprising a promoter region of the TDH3 gene was carried out using the TB2717 primer (5'-TAGCGTTGAATGTTAGCGTCAACAAC-3': SEQ ID NO: 81) and the TB 1928 primer (5'-TTTGTTTGTTTATGT-GTGTTTATTCGAAAC-3': SEQ ID NO: 82). PCR to amplify the DNA fragment comprising a terminator region of the URA3 gene was carried out using the TB2121 primer (5'-TGCATGTCTACTAAACTCACAAATTA-GAGCTTCAATT-3': SEQ ID NO: 83) and the TB 1672 primer (5'-GTCGACCAAGTTAGCTGGGGG-TAATAACTGATATAATTAAA-3': SEQ ID NO: 84). PCR to amplify the DNA fragment comprising part of the PDC1 gene was carried out using the TB2814 primer and the TB0115 primer.

In addition, the phleomycin resistant gene was amplified via PCR using pBBLE-LDHKCB (Applied and Environmental Microbiology, 71, 2789-2792) as a template. PCR was carried out using the TB2100 primer (5'-ACATAAACAAA-CAAAATGACCGACCAAGCGACG-3': SEQ ID NO: 85) and the TB0897 primer (5'-AGTTTAGTAGACATGCAT-CATGAGATGCCTGCAAG-3': SEQ ID NO: 86).

Furthermore, a linear DNA fragment cleaved at a site approximately 700 bp upstream on the 5' side of the PDC6 gene was amplified via PCR using pCR-5U_PDC6 as a template. PCR was carried out using the TB2105 primer (5'-CTGCGGCCGGCCGCACTTCCAAGCATCT-CATAAACC-3': SEQ ID NO: 87) and the TB4031 primer (5'-ACATAAACAAACAAAGATGTACGATCGC-CTGCAC-3': SEQ ID NO: 88). The DNA fragment obtained via PCR, the DNA fragment comprising a terminator region of the HIS3 gene, and the DNA fragment comprising a promoter region of the TDH3 gene were subjected to cloning using the In-Fusion™ Advantage PCR Cloning Kit, and the resulting plasmid was designated as pCR-5U_PDC6-T_HIS3-P_TDH3-3U_PDC6.

Subsequently, a linear DNA fragment cleaved between a promoter region of the TDH3 gene and the 5' upstream untranslated region of the PDC6 gene was amplified via PCR using pCR-5U_PDC6-T_HIS3-P_TDH3-5U_PDC6 as a template. PCR was carried out using the TB1928 primer and the TB2118 primer (5'-GACGGTTCTTTGCAAGATGTAC-GATCGCCTGCAC-3': SEQ ID NO: 89). The DNA fragment obtained via PCR, the DNA fragment comprising a terminator region of the URA3 gene, the phleomycin resistant gene, and the DNA fragment comprising part of the PDC1 gene were subjected to cloning using the In-Fusion™ Advantage PCR Cloning Kit, and the resulting plasmid was designated as pCR-5U_PDC6-T_HIS3-P_TDH3-Ble-T_URA3-PDC1 part-5U_PDC6.

All publications, patents, and patent applications cited herein are incorporated herein by reference in their entirety.

The invention claimed is:

1. A method for producing isobutanol, comprising the steps of:
   (1) culturing a recombinant yeast strain comprising the isobutanol biosynthesis pathway, in which an NADP-dependent isocitrate dehydrogenase gene is overexpressed in the cytoplasm, and
   (2) obtaining isobutanol from the culture,
      wherein said NADP-dependent isocitrate dehydrogenase gene encodes a protein selected from the group consisting of (a) and (b):
      (a) a protein comprising the amino acid sequence of SEQ ID NO: 2; and
      (b) a protein comprising an amino acid sequence having 90% or higher sequence identity with the amino acid sequence of SEQ ID NO: 2, and having NADP-dependent isocitrate dehydrogenase activity,
      wherein the recombinant yeast strain comprises genes encoding enzymes which are involved in the conversion of pyruvate to 2-keto-isovalerate in the isobutanol biosynthesis pathway, and wherein said enzymes are expressed in the cytoplasm of said recombinant yeast strain.

2. The method for producing isobutanol according to claim 1, wherein the recombinant yeast strain lacks the NAD-dependent isocitrate dehydrogenase gene that functions in the cytoplasm.

* * * * *